United States Patent
Villa et al.

(10) Patent No.: US 6,645,767 B1
(45) Date of Patent: Nov. 11, 2003

(54) CELLS ENGINEERED TO CONTAIN GENES OF INTEREST WITHOUT EXPRESSED BACTERIAL SEQUENCES AND MATERIALS AND METHODS THEREFOR

(75) Inventors: Manuel J. Villa, Ithaca, NY (US); Susan A. Henry, Ithaca, NY (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 09/678,339

(22) Filed: Oct. 3, 2000

(51) Int. Cl.[7] ............................. C12N 1/14; C12N 1/16; C12N 15/00; C12N 15/09; C12N 15/74
(52) U.S. Cl. ............... 435/483; 435/254.2; 435/254.21; 435/320.1; 435/255.2; 568/833
(58) Field of Search ................................. 435/134, 155, 435/254.2, 254.21, 320.1, 483, 255.2; 568/833

(56) References Cited

U.S. PATENT DOCUMENTS

| | | | |
|---|---|---|---|
| 2,112,553 A | 3/1938 | Bartow et al. ............... | 568/833 |
| 5,296,364 A | 3/1994 | Agrawal et al. ............. | 435/155 |
| 5,529,912 A | 6/1996 | Henry et al. ................. | 435/155 |
| 5,599,701 A | 2/1997 | Henry et al. ................. | 435/155 |
| 5,618,708 A | 4/1997 | Shirai et al. ................. | 435/155 |
| 5,626,847 A | 5/1997 | Agrawal et al. ......... | 424/195.1 |
| 5,637,504 A * | 6/1997 | Hinchliffe et al. | |
| 5,646,037 A * | 7/1997 | Buxton | |
| 5,844,089 A * | 12/1998 | Hoffman et al. | |

OTHER PUBLICATIONS

Vincent Sanchis et al. A recombinase–Mediated System for Elimination of Antibiotic Resistance Gene Markers from Genetically Engineered *Bacillus thuringiensis* Strains Applied and Environmental Microbiology Feb. 1997 p. 779–784 American Society for microbiology.*
Michael A Romanos et al. Foreign Gene Expression in Yeast: a Review Yeasr vol. 8: 423–488.*
Sutcliffe, J.G., et al., *Proc. Natl. Acad. Sci. U.S.A.* 75:3737 (1978).
Levy, S.B., *Scientific American*, Mar. 1998, pp. 46–53.
http://biosafety.ihe.be/ (2001).
http://www.europa.eu.int/comm/food/index_en.html (2000).
http://www.vm.cfsan.fda.gov/~dms/opa–micr.html (1998).
21 C.F.R. 184.1370(c).
Bartow, E., et al., *Ind. Eng. Chem. 30*: 300 (1938).
White, M.J., et al., *J. Biol. Chem. 266*: 863 (1991).
Hall, M.N., et al., *Cell 36*: 1057 (1984).
Sambrook, Jr., et al., *Molecular Cloning: A Laboratory Manual*, 2nd Ed., Cold Spring Harbor Laboratory, Cold Spring Harbor, NY (1989) pp. 1.3–1.5, 1.13.
Hershfield, V., et al., *Proc. Natl. Acad. Sci. USA 71*: 3455 (1974).
Clarke, L., et al., *J.Mol. Biol. 120*: 517 (1978).
Hanahan, D. (1983) *J. Mol. Biol. 166*: 557.
Ito, H., et al., *J. Bacteriol. 153*: 163 (1983).
Hirsch, J.P., et al., *Mol. Cell. Biol. 6*: 3320 (1986).
Greenberg, M. L., et al., *Genetics 100(1)*:19 (1982).
Brachmann, C.B., et al., *Yeast 14*: 115 (1998).
Jones, J.S., et al., *Yeast 6*: 363 (1990).
Greenberg, M., et al., *Mol. Gen. Genet. 186*: 157 (1982).

* cited by examiner

*Primary Examiner*—James Ketter
*Assistant Examiner*—Konstantina Katcheves
(74) *Attorney, Agent, or Firm*—Reed Smith LLP

(57) ABSTRACT

Methods and materials are provided for stably introducing any gene into a specific locus in the genome of a microorganism such as yeast without the addition of any drug resistance genes. Specifically provided herein are new genetically engineered inositol-overproducing *Saccharomyces cerevisiae* strains obtained by using a novel set of yeast integration plasmids that allow the safe, stable, and controlled introduction of homologous as well as heterologous genes into the host genome. In particular, specific loci of the *S. cerevisiae* yeast genome can be targeted with single or multiple copies of a specific gene that is desired to be expressed or a given set of specific genes that the host can use without the addition of any drug resistance genes. The principles of this new methodology can also be used for the construction of other recombinant yeast and bacterial strains as well as higher eukaryotic cells.

62 Claims, 14 Drawing Sheets

CELLS ENGINEERED TO CONTAIN GENES OF INTEREST WITHOUT EXPRESSED BACTERIAL SEQUENCES AND MATERIALS AND METHODS THEREFOR

ACKNOWLEDGEMENT

The present invention was developed in part with government support under grant number GM-19629 awarded by the National Institutes of Health. The government has certain rights in this invention.

FIELD OF THE INVENTION

The present invention relates generally to materials and methods for engineering microorganisms such as yeast and bacteria whereby single or multiple copies of endogenous or exogenous genes of interest may be added to the microorganism without adding drug resistance gene markers by using a novel suite of recombinant yeast integration plasmids. Specifically, the methods and materials of this invention may be used to produce new strains of yeast which overproduce inositol but which lack drug resistance gene markers. The resulting recombinant microorganism does not contain any drug resistance gene markers and in the case of yeast the genetically modified organism could be considered "generally recognized as safe" ("GRAS") if only endogenous Saccharomyces cerevisiae or other GRAS organism genes are introduced.

BACKGROUND

Biosafety of genetically modified microorganisms for uses in human food, animal feed or plant fertilizers is a major issue to be considered in the development and application of emerging biotechnologies. The United States, Europe, and Japan are especially sensitive to the potential biohazards from foods and additives from biotechnological sources. Most of the current recombinant DNA processes use circular DNA molecules called plasmids as cloning vectors to introduce homologous or heterologous genetic information into microorganisms such as bacteria, yeast, plant, and animal cells. Plasmids have the advantage that they exist normally in prokaryotic and lower eukaryotic cells in single or multimeric forms, which means that a certain gene located on such a plasmid could exist in the cell in multicopy form, which may result in a higher expression of the proteins encoded by these genes. In such instances plasmids serve as vectors on which the new genetic property or properties can be engineered and then be subsequently transferred into a host cell. In order to detect whether such a transfer has been successful and also to maintain the plasmid in the transformed cell, the plasmids must also contain a so-called selection gene marker. A selection gene marker is typically a gene that confers resistance to an antibiotic or another substance that kills or prevents the growth of cells that do not contain such a plasmid. A selection marker can also confer other phenotypic traits that can be selected such as the color of colonies, a new enzymatic activity, as well as others.

Plasmid vectors can be replicated in the host cell if they contain autonomous replication sequences recognized by the host DNA synthesis machinery, or if they are able to integrate in the genome of the host cell. The first type of such plasmids, also known as episomal plasmids, can be amplified in large numbers inside a single host cell and their replication is independent of the host chromosomal replication during the cell cycle. The other type of such plasmids, also known as integrative plasmids, can only be replicated and maintained if they are integrated into the host cell genome. Many plasmid vectors used to transform eukaryotic host cells are known as shuttle episomal vectors, meaning that they contain prokaryotic and eukaryotic DNA sequences that allow their episomal amplification in either type of host cells. There are also combinations of prokaryotic-episomal/eukaryotic-integrative shuttle vectors.

The DNA amplification step of all episomal plasmid vectors required to transform eukaryotic cells is preferably carried out in bacterial hosts due to their faster growth rate and ease of purification of the plasmidic DNA. Most plasmids used in molecular biology (such as pBR and pUC-derived plasmids) contain as a selection marker the bacterial drug resistance marker for the amp$^r$ or bla gene (See, Sutcliffe, J. G., et al., *Proc. Natl. Acad. Sci. U.S.A.* 75:3737 (1978), the disclosure of which is incorporated herein by reference). The bla gene encodes an enzyme named TEM-1, which is a widespread plasmidic β-lactamase for narrow-spectrum cephalosporins, cefamandole, and cefoperazone and all the anti-gram-negative-bacterium penicillins except temocillin.

Unfortunately, when using the most common recombinant DNA plasmid vectors to transform microorganisms these drug resistance gene markers are inherently transferred along with the gene or genes that are of interest to the host microorganism. Consequently there is potential for the transfer of bacterial drug resistance genes from a genetically modified organism ("GMO") used as a feed additive to a wild or pathogenic bacteria that is present in the normal intestinal flora of the animal being fed, thereby transforming the normal microbial flora of the animal into new and potentially dangerous antibiotic resistant strains. For example, the TEM-1 enzyme was first reported in 1965 from an *E. coli* isolate and is now the most common β-lactamase found in enterobacteria. Resistance in more than 50% of Amp$^r$ *E. coli* clinical isolates is due to TEM-1.

The world is currently facing similar problems due to indiscriminant overuse or misuse of antibiotics to treat common human and animal illnesses. This overuse/misuse has created drug resistance in bacterial strains that are no longer responsive to available antibiotics. See, Levy, S. B., *Scientific American*, March 1998, pp. 46–53, the disclosure of which is incorporated herein by reference. The FDA as well as the World Health Organization (WHO) and European regulatory agencies are concerned about biotechnology-derived products that could lead to the uncontrolled dissemination of drug resistance genes into the environment, hence posing a potential health problem. Therefore, genetically engineered organisms, for example, recombinant yeast containing bacterial drug resistance gene markers are considered potentially biohazardous and could not be used as food or as a feed additive without carrying out a comprehensive health and environmental risk assessment for its use.

Another disadvantage of plasmids that contain bacterial antibiotic selection gene markers for use in human or animal food fermentation is that antibiotics are costly and they must be present in the medium in which the bacterial host has to be cultivated. In response to this problem "food-grade" vectors have been developed. See, for example, U.S. Pat. No. 5,627,072, the disclosure of which is incorporated herein by reference.

In the specific case of yeast, and in particular those of the genus Saccharomvces, a recombinant molecule containing a drug resistance gene marker would not be considered "generally recognized as safe" ("GRAS") by the Food and Drug Administration and would be considered to be a potential biohazard unless a risk assessment is performed on the recombinant yeast. The GRAS classification is important when choosing a microorganism to industrially manufacture a product such as inositol that is also GRAS (see, 21 C.F.R. 184.1370(c)), since a byproduct of the fermentation is the yeast biomass itself or its extract. Therefore, if the yeast biomass is biohazard-free, it can itself be sold for profit as a valuable feed or food additive, which is the case for the genus Saccharomyces. Conversely, a non-GRAS biomass, such as certain yeasts of the genus Candida, for example, *Candida boidinii*, can be considered biohazardous waste, and therefore such biomass has to be disposed of by costly procedures which add to the production cost and which could potentially impact the environment. Currently, biohazardous biomass has to be either incinerated or disposed of according to the NIH guidelines for the treatment of biohazardous waste. Therefore, having a "GRAS" regulatory status is an important aspect to be considered for a successful industrial biotechnology process.

Fermentation technology can produce many compounds at a lower manufacturing cost than the present chemical technologies, with the added advantage of being environmentally safe. Such an example is the production of inositol and inositol-containing metabolites. Industrial methods to produce inositol have been based on chemical conversion of phytic acid (inositol hexaphosphoric acid ester) to myo-inositol and phosphate using corn mill factory steep water. See, Bartow, E., et al., *Ind. Eng. Chem.* 30:300 (1938) the disclosure of which is incorporated herein by reference. The first practical industrial methods, still in use in Asia today, involve the breakdown of phytic acid with high heat, high pressures, and very acidic conditions. See, U.S. Pat. No. 2,112,553, the disclosure of which is incorporated herein by reference. Such processes produce waste products that impact the environment thereby adding to production costs due to the necessity, for treatment procedures of such waste byproducts.

Inositol, or more specifically, the most abundant isomer, myo-inositol, is presently used in non-milk based infant formula, premixed vitamin supplements for humans, and is used as feed additive for animals and aquaculture applications. Recently, however, new uses for inositol have been suggested for alternative treatments of human diseases such as diabetes type II, folate-resistant neural tube defects (NTDs), manic depressive disorders, and obsessive compulsive disorders ("OCD's").

Inositol and inositol derivatives can be produced by fermentation of genetically modified yeast. White, M. J., et al., *J. Biol. Chem.* 2:863 (1991), (hereinafter referred to as "White, et al. (1991)"), and U.S. Pat. Nos. 5,529,912 and 5,599,701, the disclosures of which are incorporated herein by reference, describe genetically modified yeast of the genus Saccharomyces which has a functional stable recombinant DNA sequence that prevents the expression of the OPI1 gene, a negative regulator of phospholipid biosynthesis which results in the overexpression and excretion of inositol. There is described therein a complete deletion of the open reading frame ("ORF") region of the OPI1 gene, which results in the constitutively depression of the gene INO1, the result of which is the overproduction and excretion of inositol and overproduction of inositol-containing metabolites and/or phospholipids. Many of the other coregulated enzymes involved in phospholipid biosynthesis are also expressed at high levels. Using these methods, a diploid Opi⁻ strain with its two endogenous copies of the INO1 gene was constructed accordingly (See, U.S. Pat. No. 5,599,701), designated as the YS2 strain, and was deposited at the American Type Culture Collection located at 10801 University Boulevard, Manassas, Va., under accession number 74033. U.S. Pat. No. 5,529,912 further describes an Opi⁻ diploid *S. cerevisiae* strain designated as YS3 (ATCC accession number 74034) containing multiple (3–6) copies of the INO1 gene. U.S. Pat. No. 5,296,364, the disclosure of which is incorporated herein by reference, describes a method for increasing production of inositol into the growth media using the *S. cerevisiae* strains designated as YS2 and YS3.

U.S. Pat. No. 5,618,708, the disclosure of which is incorporated herein by reference, describes mutants of the yeast genus Candida which excrete inositol into the growth media. Some members of the genus Candida, however, are not considered GRAS, as stated above.

However, even though wild type *S. cerevisiae* is considered a GRAS organism, new genetically modified strains such as the YS3 strain described in White, et al. (1991) and U.S. Pat. Nos. 5,529,912 and 5,599,701 is not considered to be GRAS because it contains bacterial drug resistance gene markers that were inserted in its genome during the insertion of recombinant plasmids carrying extra copies of the INO1 gene.

In order to solve the above-described limitations of the present genetic engineering technology, new recombinant DNA techniques and materials have been developed that allow for genetic metabolic engineering of yeast without adding any heterologous drug resistance genes in the DNA recombination process. They also allow for the stable integration of genes of interest into yeast, such as even more copies of the INO1 gene than has been previously possible, and the integrations are done at different loci in the genome hence increasing the genetic stability of the resulting strain. These novel recombinant strains could be considered GRAS and contain improved nutritional qualities.

SUMMARY OF THE INVENTION

Accordingly, it is a primary object of the present invention to eliminate the use of drug resistance gene markers in plasmids for genetically engineering yeast destined for human food or animal feed supplements.

Another object of the present invention is to construct recombinant microorganisms so that genes of interest are added to the host microorganism without adding any drug resistance genes or other undesirable genes as selection gene markers.

Another object of the present invention is to use *Saccharomyces cerevisiae* genes as selection gene markers for plasmid amplification in bacterial hosts, such as LEU2, which are considered GRAS.

Yet another object of the present invention is to produce a yeast of the genus Saccharomyces containing one or multiple copies of a specific endogenous yeast gene targeted to one or more different loci in the yeast genome but lacking drug resistance gene markers.

Still another object of the present invention is to produce yeast containing a group of genes that codes for enzymes that make up a step of or an entire metabolic pathway that the host yeast does not contain without adding any drug resistance gene markers.

Another object of the present invention is to provide a suite of yeast integration plasmids which can be stably integrated into a yeast genome without carrying over any drug resistance or other undesirable exogenus genes.

Another object of the present invention is to provide a suite of vectors which use non-lethal genes such as nutritional yeast genes as selectable markers for DNA amplification in bacteria or yeast and non-lethal genes such as yeast genes as targeting gene markers for integration into auxotrophic yeast strains.

Another object of the present invention is to provide a recombinant yeast cell of the genus Saccharomyces that is free of drug resistance genes that overproduces inositol and inositol metabolites at levels above those of any other yeast strains.

Still yet another object of the present invention is to provide yeast that is enriched as to inositol, inositol-containing metabolites, phosphorylated and/or methylated forms of inositol or any of its stereoisomers, or phosphatidyl-inositols that does not contain any drug resistance genes.

Another object of the present invention is to produce prototrophic recombinant microorganisms that are free of drug resistance genes and which can be grown in minimal media without the addition of antibiotics or nutritional supplements such as amino acids.

These and other objects of the present invention are achieved by one or more of the following embodiments.

In one aspect, the invention features a method of stably inserting at least one gene of interest into a specific locus in the genome of a host haploid yeast cell without adding any drug resistance genes to the host to form a genetically modified diploid, comprising:

constructing host haploid yeast strains of opposite mating types to contain a non-lethal, selectable gene mutation, a target gene mutation, in at least one gene of either of the haploids;

constructing at least one or a suite of a plurality of yeast integration plasmids, wherein each member plasmid comprises a selection gene marker which allows for replication of the plasmid in a plasmid amplification host and for selection of the transformed colonies of the host; a targeting gene marker for directing the insertion of the plasmid into a specific mutated homologous locus, a target gene mutation, in the host yeast genome; a gene of interest that is desired to be expressed in the host yeast; and an origin of DNA replication functional in a plasmid amplification host, such that the yeast integration plasmids do not contain any drug resistance genes;

amplifying each of the yeast integration plasmids in the plasmid amplification host wherein the plasmid amplification host has a selectable phenotype which is released by the selection gene marker of the yeast integration plasmid upon its transformation into the plasmid amplification host;

purifying the amplified yeast integration plasmids;

transforming opposite mating types of the host yeast haploids with yeast integration plasmids such that a targeting gene marker of a yeast integration plasmid directs the integration of the integration plasmid to the target gene mutation in the host to which it is homologous; and mating the transformed haploid yeast cells of opposite mating types to form a diploid cell.

In another aspect, the invention features a yeast integration plasmid, comprising:

a selection gene marker;

a targeting gene marker;

a gene of interest; and an origin of DNA replication, wherein the plasmid does not contain any drug resistance genes.

In another aspect, the invention features a yeast cell of the genus Saccharomyces having an opi⁻ phenotype genetically engineered to contain one or more target gene mutations comprising ade2, his3, leu2, lys1, met15, trp1, and ura3 which cause auxotrophic phenotypes in the host which can be rescued by insertion of one or more yeast integration plasmids which carry a targeting gene marker which comprises the corresponding functional gene which is homologous to the target gene mutation in the host and which rescues the corresponding auxotrophies of the host.

In a preferred embodiment, the yeast integration plasmids carry the INO1 gene.

Other features and advantages of the invention will be apparent from the following description of the preferred embodiment, and from the claims.

DETAILED DESCRIPTION OF THE INVENTION

I. DEFINITIONS

Figure 1:
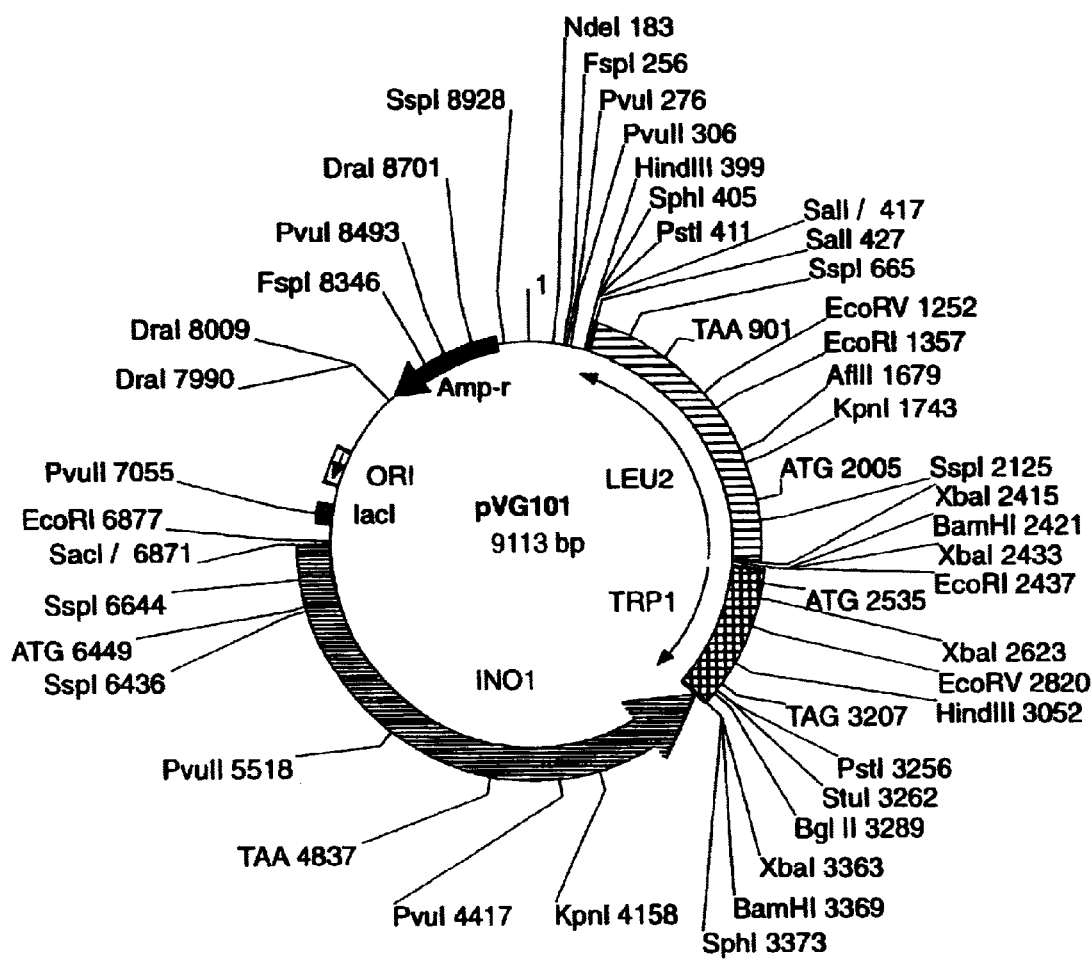
FIG. 1 is a schematic representation of yeast integration plasmid pVG101.

"Yeast integration plasmid" and "integration plasmid" refer to a plasmid for integration into yeast that carries a selection gene marker, a targeting gene marker, a gene of interest, and a DNA sequence that functions as a microorganism autonomous DNA replication start site, hereinafter referred to as an origin of DNA replication, such as ORI for bacteria, or 2 μm, ARS, or CEN for yeast. After amplification, a yeast integration plasmid that is used to transform yeast must not carry any sequences for elements such as 2 μm, ARS and/or CEN that allow autonomous DNA replication in yeast. A yeast integration plasmid can only be replicated in yeast if it has been integrated into the yeast genome by a process of DNA recombination such as homologous recombination that integrates a linear piece of DNA into a specific locus in the yeast genome. However, integration plasmids may also be constructed such that the plasmids are maintained episomally in other host cells provided that the plasmid carries an origin of replication recognized by the DNA replication machinery of that host cell. These other host cells can be higher eukaryotic cells such as plant, animal, or human cells.

A "selection gene marker" and "selection marker" refer to a gene carried on a yeast integration plasmid that confers to a transformed host a genetic advantage with respect to a host that does not contain it in that it allows for the replication and isolation of yeast integration plasmids in a host microorganism. A selection gene marker must not be a drug resistance gene. Selection gene markers must produce an easily identifiable phenotype, for example, survival in growth media lacking a particular nutrient. In the present invention a selection gene marker is preferably a yeast gene, more preferably a yeast nutritional gene such as LEU2, which allows strains containing it to be selected in a bacterial plasmid amplification host strain such as, for example, *E. coli* JA221, that is auxotrophic for the amino acid leucine.

"Targeting gene marker" and "targeting gene" refer to a functional gene carried on a yeast integration plasmid that directs the insertion by homologous recombination of the yeast integration plasmid into a specific mutated homologous locus in a yeast host called a "target gene mutation." A target gene mutation of the yeast host produces a particular non-lethal, selectable, preferably auxotrophic phenotype in the host. A targeting gene marker preferably rescues an auxotrophy in a yeast host.

"Host yeast strain," "host strain," "parent yeast is strain," "host mutant," and the like refer to haploid yeast cells to which one or more yeast integration plasmids are to be integrated.

"Gene" refers to a segment of DNA composed of a transcribable region and regulatory sequences that make transcription and translation possible and can, either alone or in combination with other genes, provide an organism with an identifiable trait.

"Phenotype" refers to a particular manifestation of a trait (physical or functional characteristic of an organism) which corresponds to the presence, absence, or mutation of a particular gene.

"Gene of interest" means a gene carried on a yeast integration plasmid that is desired to be expressed in a host yeast strain. A gene of interest can be homologous or heterologous to the host yeast genome. In the case where overproduction of inositol and inositol metabolites is desired, the gene of interest carried on a suite of yeast integration plasmids is INO1. A gene of interest can also be a member of a group of genes that codes for enzymes that make up a step of a metabolic pathway or an entire metabolic pathway if the host yeast does not have the set of genes to carry out that metabolic step or metabolic pathway. In cases where the biosafety of the host yeast is to be assured, the gene of interest is preferably of the Saccharomyces genus or other GRAS genes, but otherwise the gene of interest may be a non-GRAS yeast gene, or any genes from bacteria, plants, or animals, including humans.

"Homologous recombination" means genetic exchange between identical or nearly identical DNA sequences. A DNA plasmid such as a yeast integration plasmid that contains a yeast sequence, in the absence of elements that would allow its autonomous replication, integrates at the homologous chromosomal locus after DNA transformation. Plasmid integration is used to insert one or more stable single copies of a gene of interest at a unique chromosomal site in a host. Homologous recombination is catalyzed by recombination enzymes which direct the matching, cutting and ligating of the DNA sequences so that homologous recombination can occur between plasmid sequences and DNA sequences in the host.

"Complete gene deletion," "complete deletion" and "complete gene removal" refer to the removal of the complete open reading frame ("ORF") of a gene.

"Origin of DNA replication" refers to a sequence of DNA carried on a yeast integration plasmid which functions as a microorganism autonomous DNA replication start site, i.e., the DNA sequence at which DNA replication is initiated. In a bacterial host, replication of plasmid DNA is performed by a subset of enzymes that carry out the duplication of the bacterial chromosome. Integration plasmids that are to be amplified in a bacterial plasmid amplification host must carry a bacterial origin of DNA replication. Integration plasmids that are to be amplified in a yeast plasmid amplification host must carry a yeast origin of DNA replication which must be removed after amplification and prior to integration in a host yeast.

"Auxotroph" and "auxotrophic" refer to a mutant microorganism that, unlike the wild-type, requires the addition of a growth factor or other essential nutrients to a minimal medium for growth to occur. "Prototroph" and "prototrophic" by contrast, refer to a microorganism that is capable of growing on limited nutrients or minimal medium, such as a wild-type organism. A "nutritional auxotrophy" results from a gene mutation that renders the microorganism unable to grow in a medium lacking a particular nutrient but able to grow if the nutrient is provided.

"Drug resistance genes" or "resistance genes" refer to microorganism genes, such as bacterial $amp^r$ or bla, that give rise to proteins that shield bacteria from an antibiotic's effects.

II. METHODS AND RESULTS

According to the present invention methods and materials are provided for stably introducing any gene into a specific locus in the genome of a microorganism such as yeast without the addition of any drug resistance genes. Specifically provided herein are new genetically engineered inositol-overproducing *Saccharomyces cerevisiae* strains obtained by using a novel set of yeast integration plasmids that allow the safe, stable, and controlled introduction of homologous as well as heterologous genes into the host genome. In particular, specific loci of the *S. cerevisiae* baker's yeast genome can be targeted with single or multiple copies of a specific gene that is desired to be expressed or a given set of specific genes that the host can use without the addition of any drug resistance genes. The principles of this new methodology can also be used for the construction of other recombinant yeast and bacterial strains such as, in the case of GRAS organisms, other strains of the genus Saccharomyces (e.g., *S fragilis, Kluyveromyces lactis* (previously called *S. lactis*), and certain strains of the genus of Candida, such as *Candida lipolytica, Candida guilliermondii, Candida pseudotropicalis*, and *Candida utilis*, as well as other yeast strains that may not be GRAS if the assured biosafety of the product is not an issue. Examples of other microorganisms which are used in food and dairy fermentations include bacteria of the genus Pediococcus, Leuconostoc, Lactobacillus, Lactococcus, *Streptococcus thermophilos*, and Bacillus. The integration plasmids of the present invention can also be used to transform higher eukaryotic cells such as human, animal, and plant cells.

In particular, the methods herein provide for the construction of host yeast strains which preferably carry mutations in one or several specific metabolic pathways of the yeast which preferably yield auxotrophic host mutants incapable of survival in minimal media without supplementation with nutrients. The auxotrophies of such host mutants are rescued by transforming the host mutants with yeast integration plasmids that carry a homologous functional gene, referred to hereinafter as a targeting gene marker. In order to generate enough copies of a plasmid for transformation purposes, yeast integration plasmids are amplified in a plasmid amplification host microorganism, preferably bacteria, and the plasmids are then purified by methods well known in the art. After being linearized, the yeast integration plasmids carrying a targeting gene marker and other elements described below are then stably inserted sequentially at one or more specific mutated loci in the host genome which are the targets for homologous recombination. Since the entire yeast integration plasmid is stably inserted into the host genome, a gene of interest that is desired to be added to the host genome that is also carried on the yeast integration plasmid is stably integrated into the genome of the host yeast strain.

According to the present invention, a suite of novel yeast integration plasmids is provided in which all the gene markers and the gene of interest are preferably endogenous yeast genes. A targeting gene marker directs a yeast integration plasmid to a specific mutated homologous locus in the host yeast genome, also referred to as a target gene mutation. Each member integration plasmid of the suite has a different targeting gene marker so that each integration plasmid member is directed to a different and specific mutated locus in the host yeast genome. A selection gene marker allows a yeast integration plasmid that contains it to be replicated in a plasmid amplification host microorganism and allows for the selection of the host colony that was transformed with the plasmid. A gene of interest, also carried on a yeast integration plasmid, is any gene desired to be expressed in a host yeast strain and can be homologous or heterologous to the host genome. A gene of interest can be the same gene in all members of a suite of yeast integration plasmids, such as INO1, or a gene of interest can be one of a group of different genes coding for enzymes that make up a metabolic pathway or a step thereof. In order to facilitate the homologous recombination of a yeast integration plasmid into a targeted locus, these plasmids preferably are linearized prior to transformation by cutting the targeting gene marker internally with restriction enzymes. Each member integration plasmid of the suite is then integrated sequentially into its target gene mutated locus (target gene mutation).

As stated above, the yeast integration plasmids of the invention do not carry any drug resistance gene markers such as bacterial $amp^r$ which is a traditional gene marker used for selection of bacterial hosts containing the most common commercial plasmids. Instead, a yeast integration plasmid carries a selection gene marker, preferably a yeast gene, used for amplification and isolation of yeast integration plasmids in a plasmid amplification host microorganism such as bacteria or yeast. The selection gene marker preferably rescues a selectable auxotrophy, more preferably a nutritional auxotrophy in the replication host microorganism. In the reference example herein genes in the leucine biosynthetic pathway, more specifically the LEU2 gene, are used as a substitute for an $amp^r$ gene.

If the host yeast strain is constructed to have only one auxotrophic or other selectable mutation, such as a difference in color of the colonies, then the host is transformed with only one yeast integration plasmid. In such a case a transformed host that was auxotrophic can then be grown and maintained in a minimal selection medium without the auxotrophic nutrient. If however the host yeast is constructed to have more than one auxotrophic or other selectable mutation, then the auxotrophies caused by the mutations are rescued by a suite of yeast integration plasmids constructed so that each member of the plasmid suite carries a different targeting gene marker directed to the corresponding target gene mutation in the host. After integration of the yeast integration plasmids the prior auxotrophies of the host are rescued. Therefore a host so transformed can have multiple copies of the same gene of interest or a set of individual genes of interest stably integrated into its genome at specific mutated loci, thereby rendering the diploid strain prototrophic as long as all the auxotrophies are rescued in either one of the haploid mating types. It is to be understood that not all the auxotrophies or other selectable mutations in a host haploid need to be rescued. If the auxotrophies which remain in each haploid of opposite mating types are complementary to each other when the haploids are mated to form a diploid, then the resulting diploid is prototrophic. Thus, a prototrophic diploid strain need not have both of the specific mutated loci on both mating types integrated with targeting gene markers that are carried on yeast integration plasmids so long as each mutation causing an auxotrophy is rescued in at least one of the haploid mating types.

Finally, in the case where the genetically modified microorganism is a yeast, preferably a *S. cerevisiae* Opi$^-$ mutant, with extra copies of the gene of interest, INO1, after such yeast is fermented, a product is excreted by the genetically modified cell into the growth media, such as inositol, or is produced in the cell, such as, for example, inositol, inositol-containing metabolites, phospholipids, and phosphatidylinositol, as well as others. Fermentation processes of the type needed for inositol production are described by U.S. Pat. No. 5,296,364 and U.S. Pat. No. 5,626,847, the disclosures of which are incorporated herein by reference. The strains of *S. cerevisiae* that overproduce inositol, known as Opi$^-$ strains, which contain an opi1 gene mutation are genetically engineered according to the methods of the present invention to contain at least eight and up to about sixteen or more total copies of the INO1 gene in a diploid strain. There is no known limit to the number of integrations that can be achieved for any gene of interest.

Host Strains

Host haploid yeast strains are first constructed to contain one or more gene mutations which are non-lethal to the host and which can be selected using methods known in the art. Preferably the gene mutations are in one or more genes of the amino acid biosynthetic pathways of the host which cause an auxotrophic phenotype, such as, for example, his3, leu2, lys1, met15, and trp1 or one or more genes of the nucleotide biosynthetic pathways of the host which cause an auxotrophic phenotype, such as, for example, ade2 and ura3. The gene mutation in the host yeast that causes an auxotrophic phenotype can be a point mutation, a partial or complete gene deletion, or an addition or substitution of nucleotides. These types of mutations cause the strains to become auxotrophic mutants which, in contrast to the prototrophic wild-type strains, are incapable of optimum growth in media without supplementation with one or more nutrients. The mutated genes in the host strain can then serve as auxotrophic gene markers which later can be targets for the insertion of yeast integration plasmids. A targeting gene marker carried on a yeast integration plasmid directs precise insertion of the plasmid into a specific homologous locus in the host cell genome, also called the target gene mutation. Such integration rescues the auxotrophy caused by the target gene mutation in the host haploid cell.

The construction of mutated host yeast strains is carried out by genetic crosses, sporulation of the resulting diploids, tetrad dissection of the haploid spores containing the desired auxotrophic markers, and colony purification of such haploid host yeasts in the appropriate selection medium. All of these methods are standard yeast genetic methods known to those in the art. See, for example, Sherman, F., et al., *Methods Yeast Genetics*, Cold Spring Harbor Laboratory, N.Y. (1978) (hereinafter "Sherman, et al. (1978)") and Guthrie, C., et al. (Eds.) *Guide To Yeast Genetics and Molecular Biology* Vol. 194, Academic Press, San Diego (1991) (hereinafter "Guthrie, et al. (1991)"), the disclosures of which are incorporated herein by reference.

In the preferred embodiment of the present invention, host yeast cells, preferably *Saccharomyces cerevisiae*, are constructed to have at least one auxotrophy caused by a mutation in at least one gene of the host amino acid biosynthetic pathways. The host strain can have an auxotrophic phenotype caused by: mutated genes, such as for example, his3, leu2, lys1, met15, trp1, all of which code for enzymes in the amino acid biosynthetic pathways of the host and which are necessary for the growth and survival of the host; and mutated genes, such as for example, ade2 and ura3, which code for enzymes in the nucleotide biosynthetic pathways of the host and which are necessary for the growth and survival of the host. The present invention is, however, not limited to these particular gene mutations and includes such other mutations that are not lethal to the host and which also do not cause adverse effects for industrial fermentation, so long as the mutations can be identified by a known selection method. Mutated or auxotrophic host yeast strains must be prepared in both haploid mating types, "a" and "alpha," and both mating types are then subsequently transformed with one or more yeast integration plasmids. The transformed recombinant haploid cells of opposite mating types are then ultimately mated to form a prototrophic diploid cell.

It is also possible that a haploid host cell upon integration of the plasmids will become completely prototrophic and can be crossed to another haploid of the opposite mating type that contains at least one auxotrophy and the final product still will be a completely prototrophic diploid. Furthermore two haploids may contain insertions of the integration plasmids of the present invention and have complementary auxotrophies, hence upon crossing they will yield completely prototrophic diploids. Having a final prototrophic diploid phenotype is an advantage because this allows the diploid to grow in minimal media without adding any supplements and therefore reduces the medium cost for an industrial production of inositol. Moreover, having a diploid for industrial purposes reduces the risk of mating with wild-type haploids during the fermentation process that may change the phenotype of the genetically modified yeast.

In the exemplified embodiment of the present invention, a host yeast cell, preferably *Saccharomyces cerevisiae*, is genetically engineered to contain a complete deletion of the open reading frame of the OPI1 gene that prevents the expression of that gene, which is a negative regulator of phospholipid biosynthesis. See, White, et al. (1991) and U.S. Pat. Nos. 5,529,912 and 5,599,701 for details of construction of opi$^-$ strains. The opi$^-$ host yeast is then modified to have one or more auxotrophies that can be rescued by transformation with yeast integration plasmids which contain the functional genes homologous to those that are mutated in the host yeast cell. For example, a host yeast cell with a mutated his3 gene which results in a histidine auxotrophy can be complemented by a yeast integration plasmid containing a targeting gene marker which is a functional HIS3 gene. A host yeast cell with, for example, additional mutated genes, such as for example, ade2, leu2, lys1, met15, trp1, ura3, and others, result in auxotrophies which can be rescued by yeast integration plasmids containing as targeting gene markers the functional homologous versions of those genes. In such a case, each yeast integration plasmid of the suite additionally carries a gene of interest, such as an extra copy of the INO1 gene, or any other desired gene.

Unlike the inositol-overproducing strain YS3 which contains additional copies of the INO1 gene in a single locus in its genome, yeast integration plasmids of the present invention can be directed to more than one specific locus in the host genome. The present invention therefore provides an improved strategy with respect to the YS3 strain in that the copies of the gene of interest (INO1) carried on yeast integration plasmids are targeted to different mutated gene loci in the host genome and additionally yields a prototrophic diploid strain. This is in contrast to the YS3 strain in which all additional copies of the INO1 gene were directed to the ura3 locus and contains, in addition, the amp$^r$ gene which was carried into the host by the plasmids used for the genetic modifications. The YS3 diploid strain has also a mutated his3 gene and thus is auxotrophic for histidine.

Spreading the additional copies of the gene of interest over several loci of the host yeast genome according to the present invention is advantageous in that it increases the genetic stability of the host yeast by preventing excision of the integrated plasmids due to intramolecular recombination. The transformed host strains of the invention are free of drug resistance genes and, in the example herein, overproduce inositol and inositol metabolites at levels well above those of wild-type and any commercially available or published yeast strains. Such transformed strains are prototrophic, genetically stable, and can be grown in minimum media without antibiotics, thereby reducing environmentally harmful wasteland lowering the cost of the fermentation growth medium.

Yeast Integration Plasmids

Yeast integration plasmids of the invention are comprised of the following DNA sequences operably joined together: a selection gene marker; a targeting gene marker; a gene of interest; and a microorganism autonomous DNA start site sequence hereinafter referred to as an origin of DNA replication. It is preferred that the gene markers and genes of interest of yeast integration plasmids be of yeast origin from a genus that will preserve the GRAS status of the genetically modified host. FIGS. 1–9 are diagrams of the yeast integration plasmids used in the exemplified embodiment of the invention.

As used herein, a plasmid is an autonomously replicating extrachromosomal DNA, usually circular in shape. Plasmids can be a variety of sizes depending on the genes comprising the integration plasmids. Plasmids present in host microorganisms can carry genes encoding traits which may or may not be present on the microorganism's chromosome. Plasmids can be present in a microorganism in single or multiple copies as separate autonomously replicating units of DNA or can be integrated into a host cell's chromosome.

The sequences for the targeting gene marker, the selection gene marker, the gene of interest and the origin of replication are operably joined together and may be joined together to form yeast integration plasmids with few or no additional plasmid sequences. Alternatively, these DNA sequences can be combined with additional plasmid DNA sequences such as an additional identification sequence that can serve the purpose of identifying/fingerprinting the genetically modified organism by using polymerase chain reaction ("PCR") procedures. For example, a known non-coding identification sequence can be additionally carried by yeast that can be amplified, for example by PCR procedures, to identify the genetically modified organism such as the modified yeast strains of the present invention. In addition, if desired, integration plasmids may contain a DNA sequence that can be engineered to be recognized by multiple restriction enzymes thereby constituting a multiple cloning site ("MCS"). The DNA sequences can be joined together in any order, as long as they remain operable, and if combined with additional plasmid DNA sequences, the targeting gene marker, the selection gene marker, the gene of interest and the origin of replication sequences can also be separated from each other by other DNA sequences. The DNA sequences can be joined together using standard recombinant DNA methods such as those described by Sambrook, Jr., et al., *Molecular Cloning: A Laboratory Manual*, $2^{nd}$ Ed., Cold Spring Harbor Laboratory, Cold Spring Harbor, N.Y. (1989) (hereinafter, "Sambrook, et al."), the disclosure of which is incorporated herein by reference.

The selection gene marker allows for replication of the yeast integration plasmid in a host plasmid amplification microorganism such as bacteria or yeast and also allows for selection of the transformed host colonies containing the integration plasmids to be amplified. A gene used as a selection gene marker is preferably a yeast gene, and more preferably is a yeast gene that complements a selectable auxotrophy in a plasmid amplification host microorganism used for replication of integration plasmids. A yeast gene such as LEU2 of *S. cerevisiae* is preferred as a selection gene marker in the present invention because it is able to rescue the leucine auxotrophy of both a specific bacterial replication host, and in certain cases discussed herein, that of a host yeast which contains a mutated leu2 gene. A selection gene marker such as the LEU2 gene carried on yeast integration plasmids of the invention replaces traditional bacterial drug resistance gene markers such as $amp^r$.

A targeting gene marker carried on a yeast integration plasmid directs its stable integration to its specific homologous locus in the host strain which preferably contains a natural or engineered target gene mutation, i.e., a point mutation, a partial gene deletion, or total gene deletion. For example, a host yeast strain that carries a his3 mutated gene is complemented by the functional HIS3 targeting gene marker provided by a yeast integration plasmid resulting in the release of the host auxotrophy upon integration of the plasmid. A targeting gene marker may also additionally function as a selection gene marker for DNA plasmid amplification in bacterial or yeast plasmid amplification hosts, provided the gene is able to rescue or complement an auxotrophy of the bacterial or yeast amplification host. For example, the plasmid pVG102-A (FIG. 4) containing the LEU2 gene can be amplified in the *E. coli* JA221 bacterial host (ATCC Deposit No. 33875) which is auxotrophic for leucine. In such a case LEU2 is the selection gene marker for the plasmid amplification step. After amplification and purification, if the pVG102-A plasmid is used to transform a yeast host that is auxotrophic for leucine, then LEU2 would serve the additional purpose of a targeting gene marker. Similarly, if one uses an *E. coli* MH1066 bacterial host (see, Hall, M. N., et al., *Cell* 3:1057 (1984), hereinafter "Hall et al. (1984)," the disclosure of which is incorporated herein by reference) which is auxotrophic for leucine, tryptophan, and uracil, the LEU2, TRP1, and URA3 genes in each of the integration plasmids could also serve a dual purpose of selection gene marker and targeting gene marker in the transformation of yeast hosts with auxotrophies in any or all of these genes.

The gene of interest in the yeast integration plasmids of the invention that is desired to be expressed in the host yeast can be homologous or heterologous to the host yeast genome. In the case where the production of inositol and its metabolites are desired, the gene of interest is INO1. The gene of interest can be the same gene in each member of a suite of yeast integration plasmids such as the INO1 gene in the exemplified embodiment of the present invention, or the gene of interest can be a different gene for each member of the suite of plasmids that is desired to be expressed in yeast. This feature of the invention allows the engineering of genetically modified yeast or other hosts with either multiple copies of the same gene of interest, causing overproduction of the encoded protein, or allows the genetic engineering of new metabolic pathways or the modification of existing metabolic pathways in the chosen host. For instance, one can engineer a new pathway to produce a given metabolite that the host yeast does not produce naturally by inserting the appropriate genes to create such a novel metabolic pathway which in turn produces the metabolite. It is to be understood that it is also possible to construct yeast integration plasmids to contain more than one gene of interest in a tandem repeat configuration such that each copy of the gene of interest is in the same head to tail orientation. The exemplified embodiment of the present invention uses only the yeast's own genes as "genes of interest" to preserve the GRAS status of the gentically modified yeast. However, genes of interest can also be integrated into the host yeast genome from other species.

Yeast integration plasmids of the invention must carry an origin of DNA replication that allows yeast integration plasmids to be replicated autonomously when introduced into a plasmid amplification host microorganism, such as preferably, bacteria, or yeast. Yeast integration plasmids of the invention more preferably contain the bacterial origin of DNA replication ORI from the commercially available plasmid pUC18 (Life Technologies, Inc. Rockville, Md.). (See, review of ORI sequences in Sambrook, et al. (1989) at pp. 1.3–1.5, 1.13 and Hershfield, V., et al., *Proc. Natl. Acad. Sci.* 71: 3455 (1974), the disclosures of which are incorporated herein by reference.) In general each yeast integration plasmid carries only one origin of replication. Despite ORI being recognized and derived from bacteria its DNA sequence does not code for any protein and cannot be expressed or recognized by the transcriptional machinery of the host yeast. Thus, even though ORI allows for episomal plasmid replication in bacteria, and is able to be integrated into the yeast genome, it is not recognized by the host yeast DNA replication machinery. Therefore, the integration plasmids of the present invention can be considered safe for use in constructing a GRAS yeast. Although the ORI from pUC18 is preferred for the practice of the present invention, other bacterial origins of replication may be used. See, Sambrook, et al. (1989) at pp. 1.3–1.5.

In cases where it is desired to replicate yeast integration plasmids in yeast, a yeast origin of DNA replication such as, for example, 2 $\mu$m, ARS, or CEN can be carried on a yeast integration plasmid. However, after the integration plasmids are amplified, the yeast origin of replication must be removed from the purified integration plasmids prior to their integration into a yeast host by methods well known in the art so that they do not autonomously replicate when they are subsequently transformed into the host yeast genome. It is also within the scope of the present invention for the yeast integration plasmids to carry a shuttle vector that can be amplified in yeast or bacteria, that contains both an autonomous DNA replication sequence for bacteria such as ORI and an autonomous DNA replication sequence for yeast such as 2 $\mu$m, CEN, or ARS, however, after amplification, the yeast origin of replication must be removed from the purified plasmids.

Transformation of Yeast Integration Plasmids into Their Hosts for Episomal Amplification Yeast integration plasmids are amplified episomally in a host microorganism such as bacteria or yeast in order to have enough plasmid DNA to perform the subsequent host yeast transformation and integration steps. Preferably the yeast integration plasmids of the present invention are replicated in bacteria because of ease of purification as compared to plasmids amplified in yeast. As stated above, in such cases the yeast integration plasmids preferably contain a bacterial origin of replication such as ORI derived from the plasmid pUC18 although other bacterial origins of replication can be used. However, as stated above, in cases where it is desired to replicate yeast integration plasmids in yeast, an origin of replication for yeast can be carried on yeast integration plasmids to allow for autonomous replication of the plasmid in a yeast plasmid amplification host so long as it is removed from the amplified plasmids.

A further feature of the yeast integration plasmids of the present invention is that a selection gene marker contained in the plasmids complements a mutated gene which preferably causes an auxotrophy in the host bacteria or yeast used for DNA amplification purposes. In the present invention the preferred bacterial host strain is *E. coli* JA221 (ATCC Deposit Number 33875) (See also, Clarke, L., et al., *J. Mol. Biol.* 120:517 (1978) ("Clark, et al. (1978)"), the disclosure of which is incorporated herein by reference.) This strain is auxotrophic for leucine due to a mutated leuB6 gene. This auxotrophy can be rescued by transforming this host with a plasmid containing the yeast gene LEU2 as a selection gene marker. Yeast integration plasmids that carry the yeast selection gene marker LEU2 that are transformed into the bacterial amplification host JA221 can be selected and amplified in minimal media such as M9 (Sambrook, et al. (1989)) which lacks leucine and which is supplemented with tryptophan at a final concentration of 50 $\mu$g/ml as described by Clark, et al. (1978). In addition to JA221 other strains of bacteria can be used as hosts for plasmid amplification such as *E. coli* strain MH1066. (See, Hall, et al. (1984).) Strain MH1066 is auxotrophic for leucine, tryptophan, and uracil. These auxotrophies can be rescued by transforming strain MH1066 with yeast integration plasmids that have as their selection gene markers the yeast genes LEU2, TRP1, and URA3, respectively. For instance, if one transforms the MH1066 strain with a yeast integration plasmid containing the TRP1 gene used as a selection gene marker, the transformed MH1066 strain is grown in minimal media M9 supplemented with leucine and uracil at a final concentration of 50 $\mu$g/ml as described by Hall, et al. (1984). It is to be understood that any of the above bacterial hosts must be made competent to intake DNA by treating the bacterial host cells with the calcium chloride procedure described by Hanahan, D., et al. *J. Mol. Biol.* 166:557 (1983) (hereinafter "Hanahan, et al. (1983)"), the disclosure of which is incorporated herein by reference. In addition, the transformation of bacterial hosts can be carried out by other procedures known in the art such as electroporation. See, Sambrook, et al. (1989).

After amplification of yeast integration plasmids in bacteria, the plasmids are purified by standard methods such as those described in Sambrook, et al. (1989) or according to the instruction provided in the JETSTAR purification kit of Genomed Corp., Raleigh, N.C.

Once the auxotrophic host haploid strains of both mating types are constructed and the yeast integration plasmids are also constructed, amplified, and purified, the next step is the sequential transformation of each mating type haploid with the appropriate integration plasmid that can complement the host auxotrophy or auxotrophies. It is known that one of the most stable ways to introduce and maintain a gene of interest into a host cell is by integration of the gene by homologous recombination. Homologous recombination in the present invention consists of the insertion of an entire yeast integration plasmid, directed by its targeting gene marker, into a specific mutated target locus in the host genome, a target gene mutation, which is a mutated gene that causes an auxotrophy in the host. The target gene mutation at the target locus in the host cell and the targeting gene marker in the yeast integration plasmid are said to be homologous. For instance, a his3 mutant gene at the target locus in the host cell genome is homologous to a functional HIS3 targeting gene marker carried on an integration plasmid. Once the recombination occurs, the targeting gene marker and all other genes carried by the integration plasmid, including the gene of interest, are stably integrated into the host genome. Therefore, in haploid host cells a single copy of a gene of interest can be integrated into a specific target locus in the host genome. In order to transform the host yeast, an integration plasmid is first linearized by opening the plasmid with restriction enzymes preferably at a given restriction site within the targeting gene marker. The linearized plasmid is then transformed into the host cell and finally is successfully homologously recombined with the target locus.

Yeast strains are transformed with isolated plasmid DNA using the lithium acetate method described by Ito, H., et al., *J. Bacteriol.* 153:163 (1983) as modified by Hirsch, J. P., et al., *Mol. Cell. Biol.* 6:3320 (1986), the disclosures of which are incorporated herein by reference. Yeast strains may also be transformed by the methods described by Guthrie, et al. (1991), pp. 182–186. Where indicated, directed transformations and linearized plasmid transformations are performed by digesting plasmids at specific endonuclease restriction sites.

Preparation of Diploid Strains

After the parent haploids are transformed with the appropriate integration plasmids and colony purified in selective medium, the transformed host haploids of opposite mating types are crossed to produce prototrophic diploids that contain multiple copies of the gene of interest at precise loci in the parent host cell genome but which lack any drug resistance gene markers. The diploid host strain carries at least one copy from each haploid mating type of a single gene of interest or a set of different genes of interest that completes a homologous metabolic pathway or constitutes a new heterologous metabolic pathway. Furthermore, if a haploid auxotrophic strain with only one mutated gene acquires a functional copy of its homologous gene from an integration plasmid, the strain will become prototrophic and will grow in synthetic minimal media without additional nutritional supplementation. In addition, when haploid strains of opposite mating types, each containing different auxotrophies but complementary to one another, are crossed, the resulting diploid becomes prototrophic and able to grow in minimal growth media. That is, the functional gene copy of a haploid strain of a mating type complements the gene mutation of the opposite mating type. For industrial applications it is preferable to have diploid strains that are completely prototrophic.

The use of several different target loci in the host cell genome in the invention may be used to increase the genetic stability of the host cells which are transformed with integration plasmids of the present invention. The insertion of the yeast integration plasmids carrying genes of interest into different target loci prevents the spontaneous recircularization and excision of integration plasmids which could take place when all the plasmids are integrated in a single target locus in the host genome. This is in contrast to the Opi⁻ YS3 diploid strain (opi1Δ::LEU2/opi1Δ::LEU2 leu2-3, -112/leu2-3, -112 his3-11, -15/his3-11, -15 ura3-1 (YIp351+INO1)/ura3-1 (YIp351+INO1) MATa/MATα) described in White, et al. (1991) and U.S. Pat. No. 5,529,912 (ATCC Deposit No. 74034) which, in a haploid, contains at most two additional copies of the gene of interest, INO1, from the plasmid Yip351+INO1 integrated at the ura3 locus of the host yeast, in addition to the endogenous copy for a total of three copies (six copies for the diploid cell). The YS3 strain remains auxotrophic for histidine. The integration plasmid YIp351 also contains the URP3 yeast gene that complements the ura3-1 mutation of the host yeast. Furthermore, the plasmid YIp351+INO1 carries the bacterial ampicillin resistance gene am$^r$, hence rendering the YS3 strain non-GRAS.

However, the exemplified embodiment of the present invention allows the insertion of at least three copies of the INO1 gene at different loci per haploid in addition to the endogenous copy of the host cell. In the exemplified diploid host there is a total of eight copies of the INO1 gene at four different loci per haploid. It is to be understood that this is not the upper limit of the number of insertions of a gene of interest for the present invention. The genetic stability of the new strain is therefore greatly increased. Thus by the methods of the present invention, multiple copies of a single gene of interest such as INO1 can be integrated in different loci of the host genome, or one can integrate a set of different genes of interest, all of which integrations are at different loci in the host genome. The integration of such genes can be confirmed by the release of the prior auxotrophy of the host or any other known selection method.

The present invention therefore provides improved strains as compared to the YS3 strain in that even more copies of the gene of interest (INO1) are targeted to different loci in the host yeast genome which confers a greater genetic stability to the strains of the present invention while not adding any drug resistance genes, and can yield prototrophic strains.

Inositol Industrial Production

An aspect of a successful industrial production of inositol is the increase of the inositol titer excreted by Opi⁻ yeast strains into the fermentation media to the highest titer possible (titer=gr. of product/liter of fermented broth) thereby reducing the costly downstream processing and purification of inositol. This goal is achieved in the exemplified embodiment of the present invention by genetic modification of wild-type baker's yeast to create Opi⁻ strains and, further in the exemplified embodiment, stable integration of at least six copies of the functional endogenous INO1 gene at a minimum of three specific loci (target gene mutations) per haploid without the use of drug resistance markers, yielding a total of at least eight copies (6 inserted copies and 2 endogenous copies) of the INO1 gene in the resulting diploid strain. The resulting strain is a prototrophic diploid. Multiple plasmid integrations at a particular locus, although less stable, can account for additional inserted copies of the INO1 gene. Of course, the present invention is not so limited and host haploid S. cerevisiae strains can be constructed with additional target loci so that they contain at least seven target loci in each haploid mating type. In general however, at least one host haploid of a mating pair can be transformed with at least one yeast integration plasmid. Haploids of opposite mating types can be mated to form diploids with at least one extra copy of the gene of interest in each mating type haploid. Clearly, one can transform integration plasmids in at least one and up to the maximum number of available target loci in a host.

As stated above, an advantage of the present invention is that the preferred yeast strains are prototrophic diploids which reduce their mating with wild-type yeast haploids in an industrial fermentation setting. Therefore the loss of multicopies of the INO1 gene or the loss of the Opi⁻ phenotype are also avoided. In addition, the diploid strains of the present invention such as MVY410, which have all target loci homologously recombined with integrated plasmids, do not easily sporulate, which decreases the possibility of genetic drift by mating with wild type yeast.

The methods and improved Opi⁻ yeast strains of the present invention such as MVY410 result in an increase of the inositol titer in the growth media to levels that make the fermentation process using these strains economically viable for industrial production. Additionally, since all yeast integration plasmids carrying the INO1 gene lack any drug resistance gene markers, an inositol-overproducing recombinant yeast is produced that has enhanced genetic stability and can be considered GRAS according to present FDA regulations. This renders the recombinant biomass or its extract or subproducts as valuable feed additives. Consequently the cost of inositol production by fermentation of yeast that is genetically modified by the present invention is reduced.

The exemplified embodiment set forth below is directed to a method for continual production of inositol, inositol-containing metabolites and phospholipids preferably in *Saccharomyces cerevisiae*, although brewer's yeast can also be used. The host yeast contains a stable recombinant DNA sequence that does not allow for the encoding of a negative regulator of phospholipid biosynthesis therein. The recombinant DNA sequence more preferably does not allow for the encoding of a negative regulator of inositol or inositol containing metabolites. Preferably the recombinant DNA sequence is an OPI1 gene deletion which is created by substitution with the yeast LEU2 gene. The sequence of OPI1 and the methods for the OPI1 gene deletion are described in White, et al., (1991) and U.S. Pat. Nos. 5,599,701 and 5,529,912.

The OPI1 gene deletion causes the Opi⁻ phenotype, which results in the overproduction of inositol inside the cell. The excess intracellular inositol is in turn excreted into the growth media. This phenotype is caused by a constitutive expression of the INO1 gene, which encodes the enzyme inositol-1-phosphate synthase. This enzyme converts glucose-6-phosphate into inositol-1-phosphate that is the limiting step in the biosynthesis of inositol. The opi1 mutant was described by Greenberg, M. L., et al., *Genetics* 100(1): 19 (1982), the disclosure of which is incorporated herein by reference, and the Opi⁻ phenotype is selected with a bioassay, the "Opi test," described therein. In the exemplified embodiment the gene of interest to be stably inserted into mutant yeasts is INO1, but the invention is not limited to this gene. The insertion by homologous recombination of multiple copies of the INO1 gene into a host yeast with a deleted OPI1 gene causes the further building of the intracellular pool of inositol, inositol-containing metabolites or phospholipids and the excess intracellular inositol is excreted into the growth media. This Opi⁻ phenotype can be detected by the "Opi test" bioassay described below.

However, the OPI1 gene deletion can also be accomplished by a newer methodology described by Brachmann. C. B., et. al., *Yeast* 14: 115 (1998) (hereinafter "Brachmann, et al. (1998)"), the disclosure of which is incorporated herein by reference. Using this method an integration plasmid containing a URA3 gene and a pair of flanking DNA sequences homologous to sequences in the host locus to be deleted are constructed. The plasmids are then transformed into the host, which must have a ura3 mutation, hence, a uracil auxotroph. The transformed strain is then colony purified and grown in a uracil minus selection medium. See, Brachmann, et al. (1998). The now transformed host contains a URA3 gene and is replica plated to a medium containing 5-FOA (5-fluoroorotic acid) (Lab Scientific, Inc., Livingston, N.J.) which selects for a ura3 gene mutation. By this method one is able to select for an internal plasmid excision that translates into the complete deletion of the chosen target loci without the addition of any auxotrophic gene marker. This method is advantageous because more of the host gene loci such as the target leu2 gene marker can be used to place more copies of the "gene of interest" by integrating a plasmid such as pVG102-A of the present invention in which the gene of interest is the INO1 gene. In this instance, LEU2 in pVG102-A serves both the function of a selection gene marker and of a targeting gene marker. In addition, the methodology described by Brachmann, et. al. (1998) can be use to make null deletions of any other target sites of interest in a host such as genes that encode transcription factors which repress the expression of a chosen enzyme in a metabolic path.

The invention is further described by reference to the reference example below, however, it should be understood that many variations and modifications can be made while remaining within the spirit and scope of the invention.

REFERENCE EXAMPLE

The following sets forth the preferred materials and methods for constructing a *S. cerevisiae* diploid homozygous for the opi1 gene deletion, JAG1 containing at least two endogenous copies of the INO1 structural gene and *S. cerevisiae* strain MVY410 with multiple insertions of the INO1 gene by homologous recombination of integration plasmids. It is to be understood that according to the present invention many other Opi⁻ and other strains of Saccharomyces and other yeasts may be made which do not contain drug resistance markers.

*S. cerevisiae* JAG1 haploid yeast strains of both mating types (*S. cerevisiae* JAG1 diploid was deposited at the American Type Culture Collection, 10801 University Blvd., Manassas, Va. 20110-2209 on Dec. 16, 1999 under patent deposit designation PTA-1065), which in addition to carrying a complete deletion of the OPI1 gene, contains mutations in non-lethal genes that cause a selectable phenotype were first constructed. Selectable mutations in the HIS3, TRP1, and URA3 genes of the host amino acid and nucleotide biosynthetic pathways were introduced to Opi⁻ mutant yeasts by genetic crosses with strains carrying mutant genes his3, trp1, and ura3, to create diploids. These diploid strains were in turn sporulated, their tetrads or asci were dissected and the desired auxotrophic haploid spores were identified and colony purified in a selective media for the chosen auxotrophies. The selected auxotrophic haploid spores were further selected for their Opi⁻ phenotypes by the Opi test bioassay described below to confirm the co-segregation of the OPI1 gene deletion and the desired auxotrophies. General methods for genetic crosses, yeast sporulation, tetrad dissection and auxotrophic spore selection are described in Guthrie, et al. (1991).

For bacterial transformations and maintenance of plasmids, *Escherichia coli* JA221 [F⁻ hsdR lacY leuB6 trpE5 recA1 lambda⁻] (ATCC Deposit Number 33875) and described in Clarke, L., et al., *J. Mol. Biol.* 120:517 (1978), the disclosure of which is incorporated herein by reference, was used.

The genotypes and sources of *Saccharomyces cerevisiae* strains used are presented in Table 1 below.

TABLE 1

| | |
|---|---|
| AID (diploid)* | ade1/ade1 ino1-13/ino1-13 MATa/MATα |
| W303 (diploid) | ade2-1/ade2-1 can1-100/can-100 his3-11,-15/his3-11, -15 leu2-3, -112/leu2-3, -112 trp1-1/trp1-1 ura3-1/ura3-1/MATa/MATα |
| JAG1 (diploid)** | his3-11, -15/his3-11, -15 leu2-3, -112/leu2,3,-112 opi1Δ::LEU2/opi1Δ::LEU2 ura3-1/ura3-1 trp1-1/trp1-1 MATa/MATα |
| MVY410 (diploid) | his3-11, -15::pVG105-A/his3-11, -15::pVG105-A leu2-3. -112/leu2-3, -112 opi1Δ::LEU2/ opi1Δ::LEU2 trp1-1::pVG104-A/trp1-1::pVG104-A ura3-1::pVG103-A/ura3-1::pVG103-A MATa/MATα |

*Available upon request from Dr. Susan A. Henry.
**ATCC patent deposit designation PTA-1065.

Table 2 describes the genes contained in each plasmid construction:[1]

TABLE 2

| Plasmid | Genes |
|---|---|
| pNO101[1] | INO1, TRP1, and amp^r |
| pJJ217[2] | HIS3, and amp^r |
| pJJ244[2] | URA3, and amp^r |
| pJJ250[2] | LEU2, and amp^r |
| pVG101[3]* (FIG. 1) | LEU2, TRP1 and amp^r |
| PVG102[3]† (FIG. 2) | INO1, LEU2 and amp^r |
| pVG102-H[3]† (FIG. 3) | INO1, LEU2 and amp^r |
| pVG102-A[3] (FIG. 4) | INO1 and LEU2 |
| pVG103[3] (FIG. 5) | INO1, LEU2, URA3 and amp^r |
| pVG103-A[3] (FIG. 6) | INO1, LEU2 and URA3 |
| pVG104[3] (FIG. 7) | INO1, LEU2, TRP1 and amp^r |
| PVG104-A[3] (FIG. 8) | INO1, LEU2 and TRP1 |
| PVG105-A[3] (FIG. 9) | INO1, HIS3 and LEU2 |

[1]Plasmid pNO101 was obtained from the plasmid collection of Dr. Susan A. Henry and is available upon request.
[2]Jones, J. S., et al., Yeast 6:363 (1990), the disclosure of which is incorporated herein by reference.
[3]FIGS. 1 to 9 show detailed maps of the pVG family of plasmids.
*Plasmid pVG101 in host *E. coli* NM522 was deposited at the American Type Culture Collection, 10801 University Blvd., Manassas, VA 20110-2209 on Dec. 16, 1999 under patent deposit designation PTA-1064
†Plasmid pVG102-H is the same as plasmid PVG102 but lacks a Hind III restriction site.

All DNA manipulations were carried out as described by Sambrook, J., et al. (1989). Unless otherwise indicated restriction enzymes were from New England Biolabs, Beverly, Mass. and the conditions of this manufacturer were followed to perform the enzyme digestion of the plasmids. Unless otherwise indicated molecular biology chemicals, amino acids and agarose were purchased from Fisher Scientific (Pittsburgh, Pa.). Media components and supplements were purchased from DIFCO Laboratories (Detroit, Mich.). All other general purpose chemical were purchased from Sigma Chemical Co. (St.Louis, Mo.).

The following growth media and genetic methods were also used. *E. coli* JA221 cells (ATCC No. 33875) used to propagate plasmid DNA containing the amp$^r$ gene (FIGS. 1–3, 5, and 7) were grown in LB medium (See, Sambrook, et al. (1989)) containing a final concentration of 50 μg/ml of ampicillin. JA221 cells which were grown to propagate plasmid DNA without the amp$^r$ gene, but with the yeast LEU2 selection gene marker (FIGS. 4, 6, 8, and 9) were grown in minimal medium M9+Trp (M9 is per liter: Na$_2$HPO$_4$, 6 g; KH$_2$PO$_4$, 3 g; NaCl, 0.5 g; NH$_4$Cl, 1 g; 2 ml of 1M MgSO$_4$; 10 ml of 20% glucose; 0.1 ml of 1M CaCl$_2$ and supplemented with tryptophan to a final concentration of 50 μg/ml adjusted at pH=7.4). All bacterial strains were incubated at 37° C. with continuous shaking at 220 rpm.

Media used for growth and sporulation of yeast have been described by Sherman, et al. (1978). For routine culture, YEPD medium (1% yeast extract, 2% peptone, 2% glucose) was used. The synthetic complete medium contained per liter: glucose, 20 g; vitamin-free yeast nitrogen base (Difco), 6.7 g; biotin, 2 μg; calcium pantothenate, 400 μg; folic acid, 2 μg; niacin, 400 μg; p-aminobenzoic acid, 200 μg; pyridoxine hydrochloride, 400 μg; myo-inositol, 2 mg; lysine, 20 mg; arginine, 20 mg; methionine, 20 mg; threonine, 300 mg; tryptophan, 20 mg; leucine, 60 mg; histidine, 10 mg; adenine, 20 mg; uracil, 40 mg; and agar (for plates only), 20 g. The auxotrophic gene markers leu2, his3, trp1 and ura3, were checked on selection medium lacking a single component (leucine, histidine, tryptophan, and uracil respectively) of the complete medium. Such medium ate named "drop-out medium," for instance, the His-drop out medium is the complete medium minus histidine. Inositol-free medium (I$^-$) is identical to synthetic complete medium with the exception that myo-inositol has been omitted. In all work involving *S. cerevisiae*, cultures were incubated at 30° C. and for liquid media the cultures were continuously shaken at 220 rpm.

Bacterial strain *E.coli* JA221 were transformed with plasmid DNA following the calcium chloride procedure described by Hanahan, et al. (1983).

Figure 2:
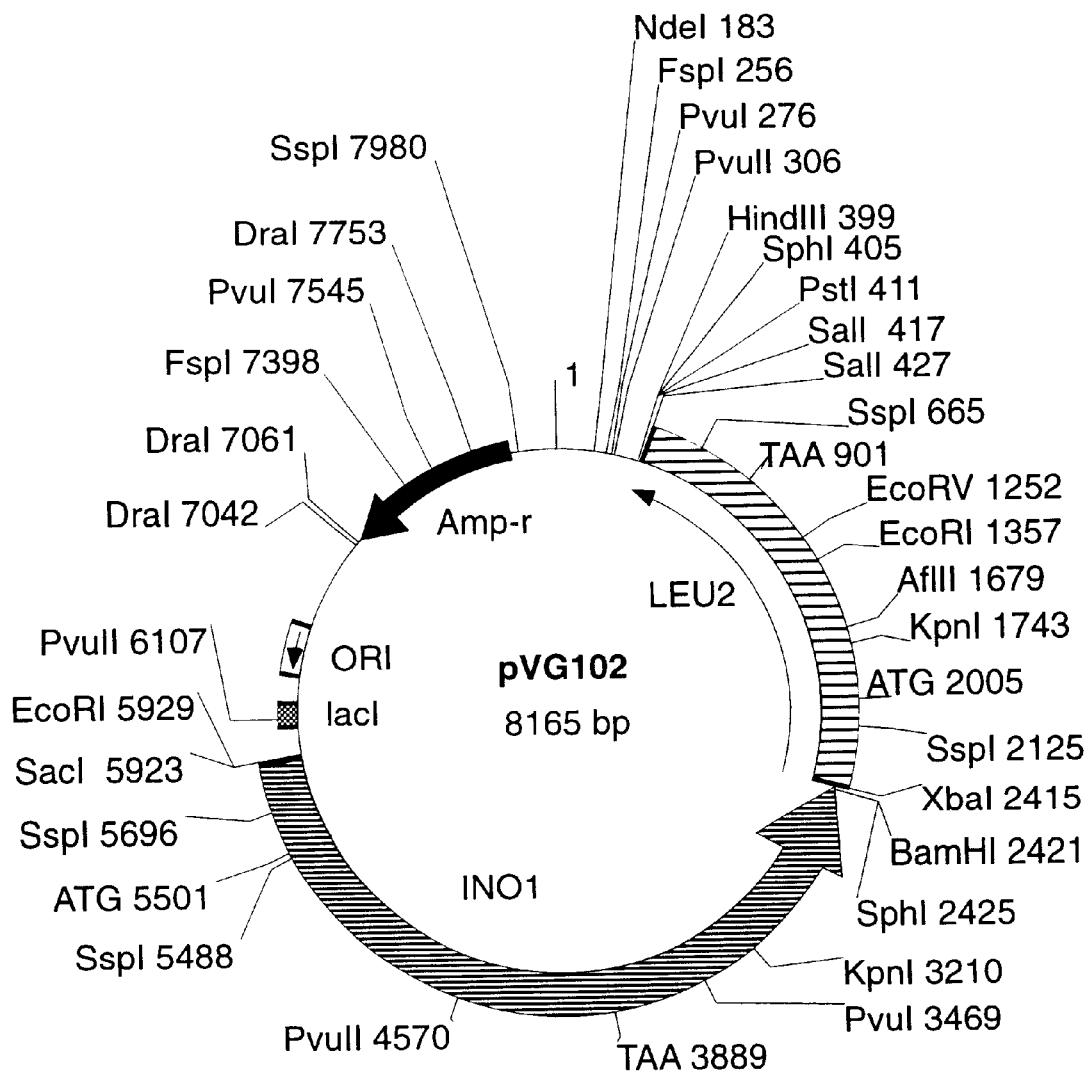
FIG. 2 is a schematic representation of yeast integration plasmid pVG102.
Figure 3:
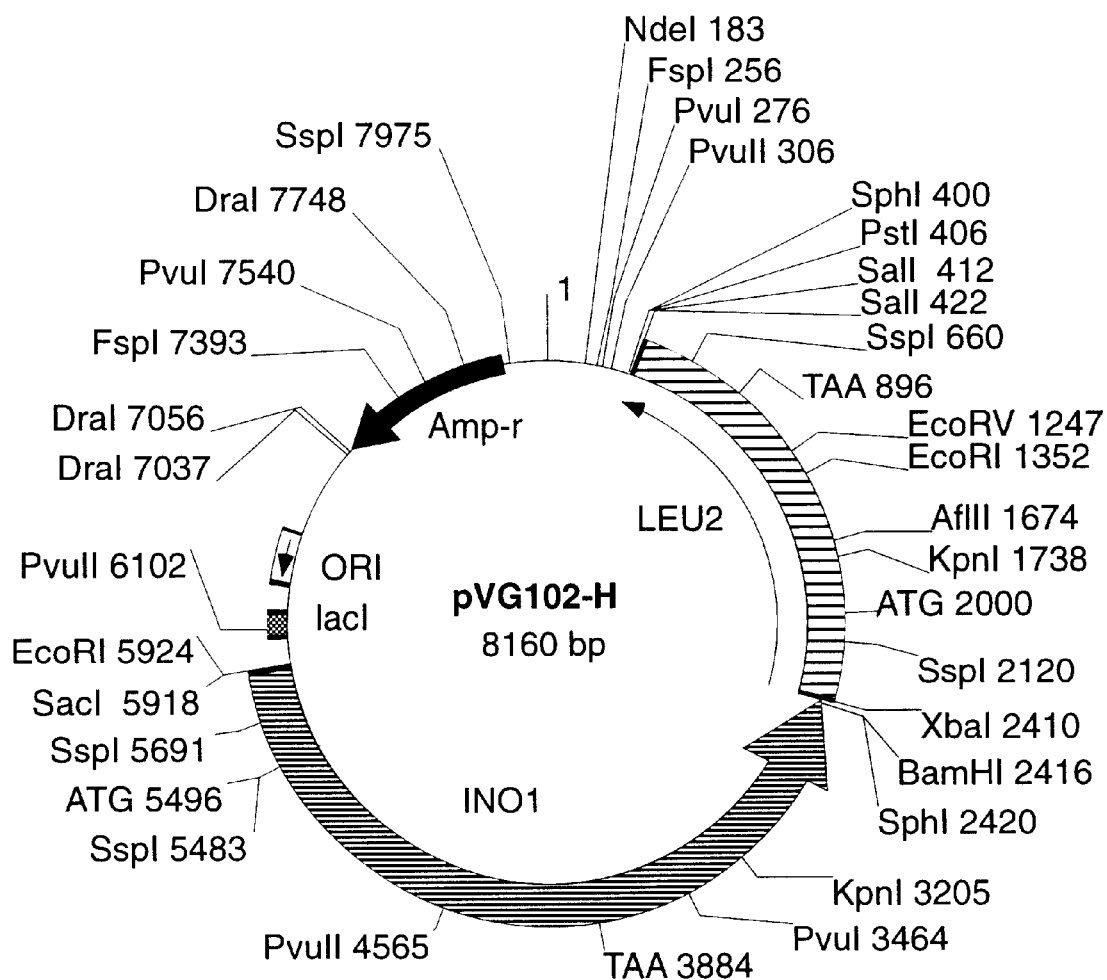
FIG. 3 is a schematic representation of yeast integration plasmid pVG102-H.
Figure 4:
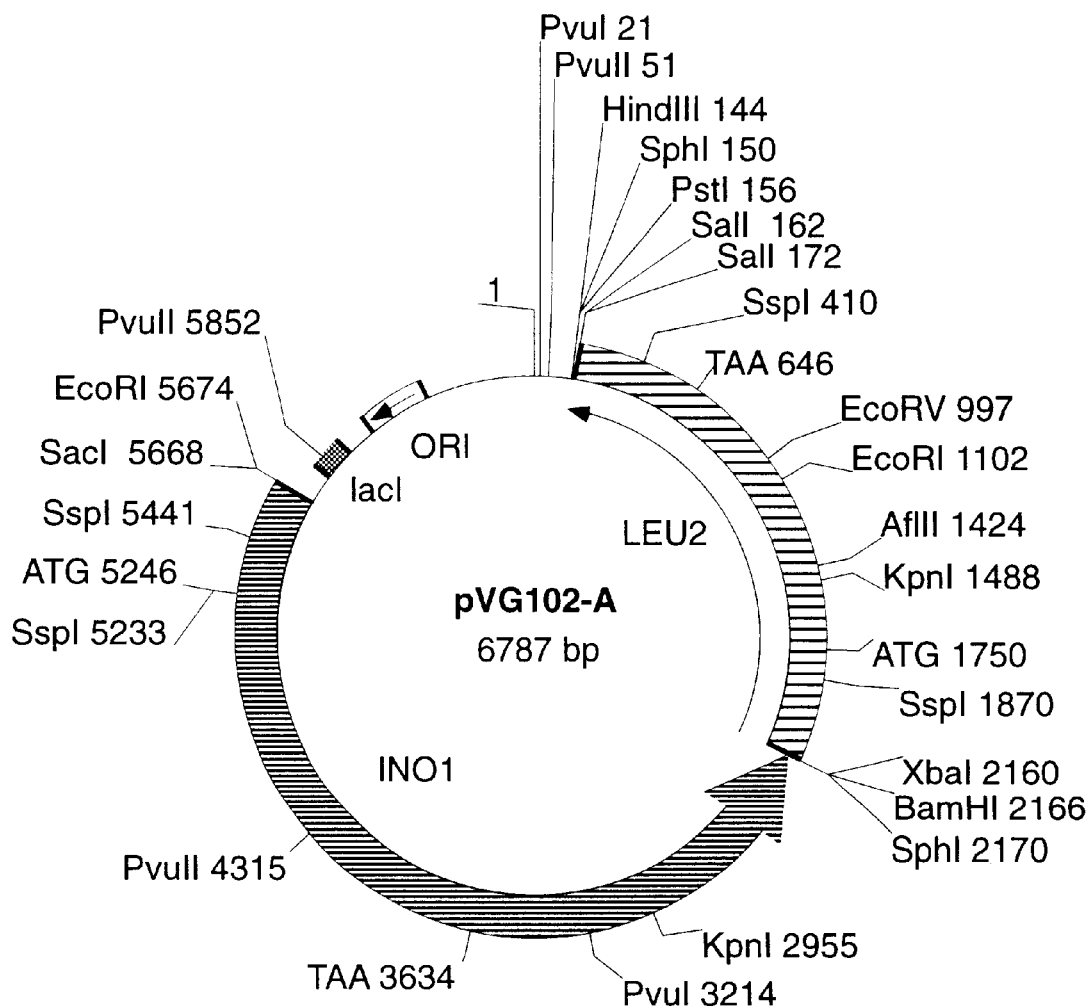
FIG. 4 is a schematic representation of yeast integration plasmid pVG102-A.
Figure 5:
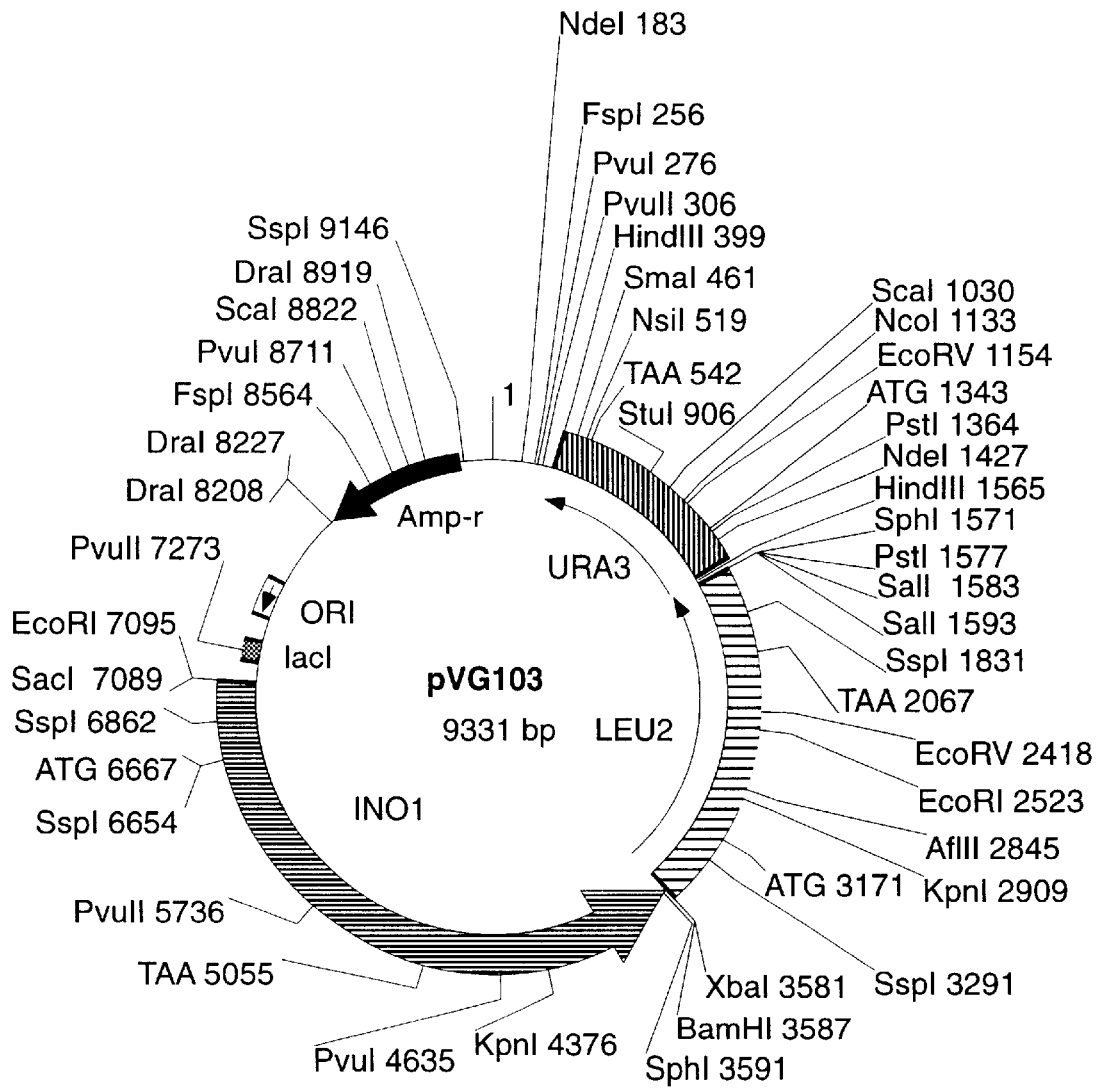
FIG. 5 is a schematic representation of yeast integration plasmid pVG103.
Figure 6:
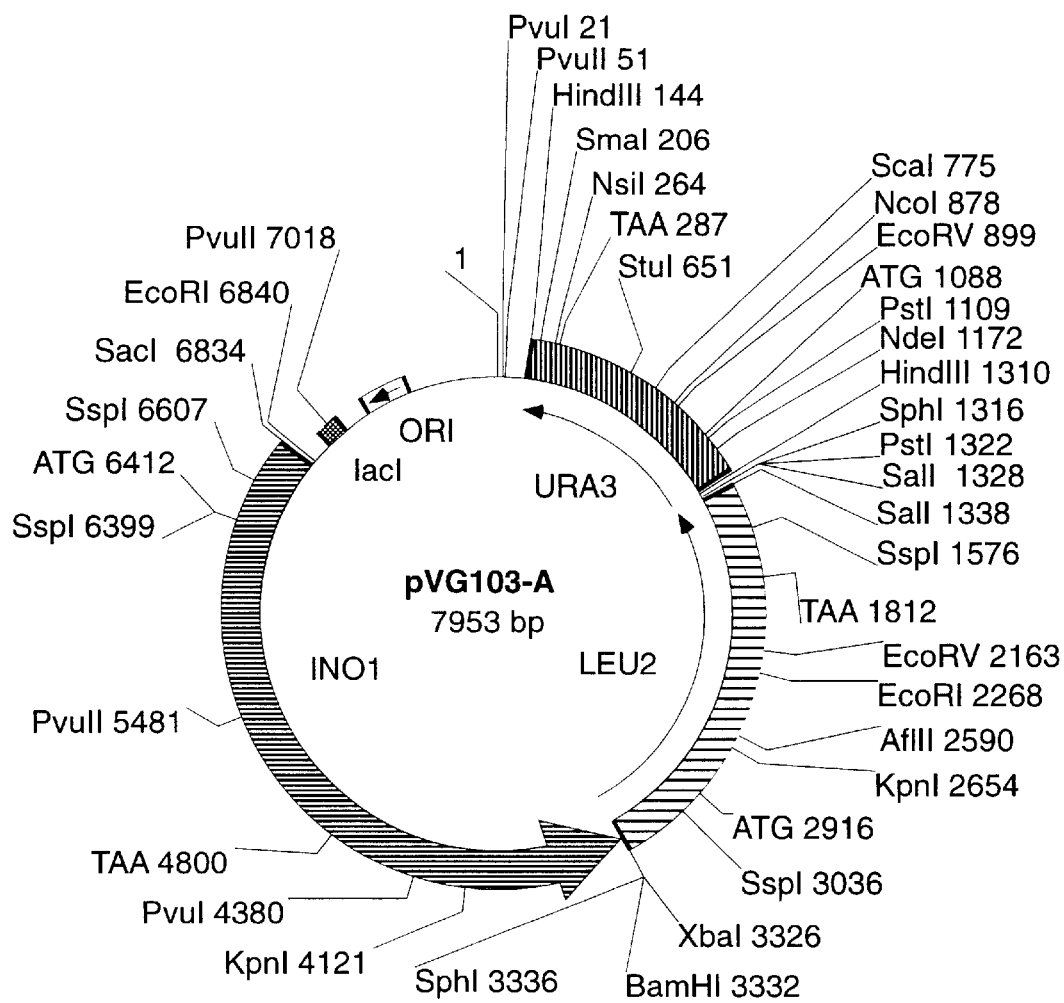
FIG. 6 is a schematic representation of yeast integration plasmid pVG103-A.
Figure 7:
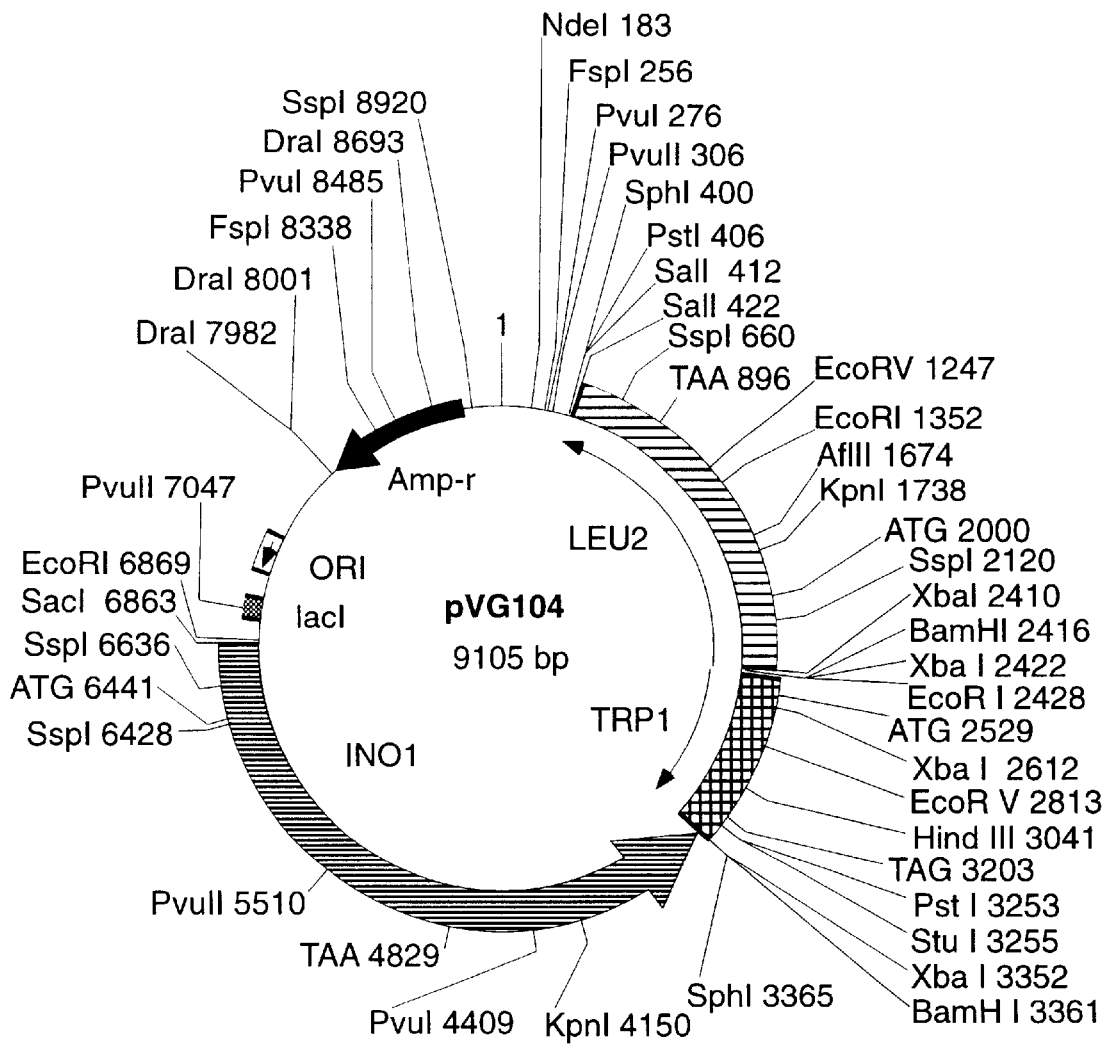
FIG. 7 is a schematic representation of yeast integration plasmid pVG104.
Figure 8:
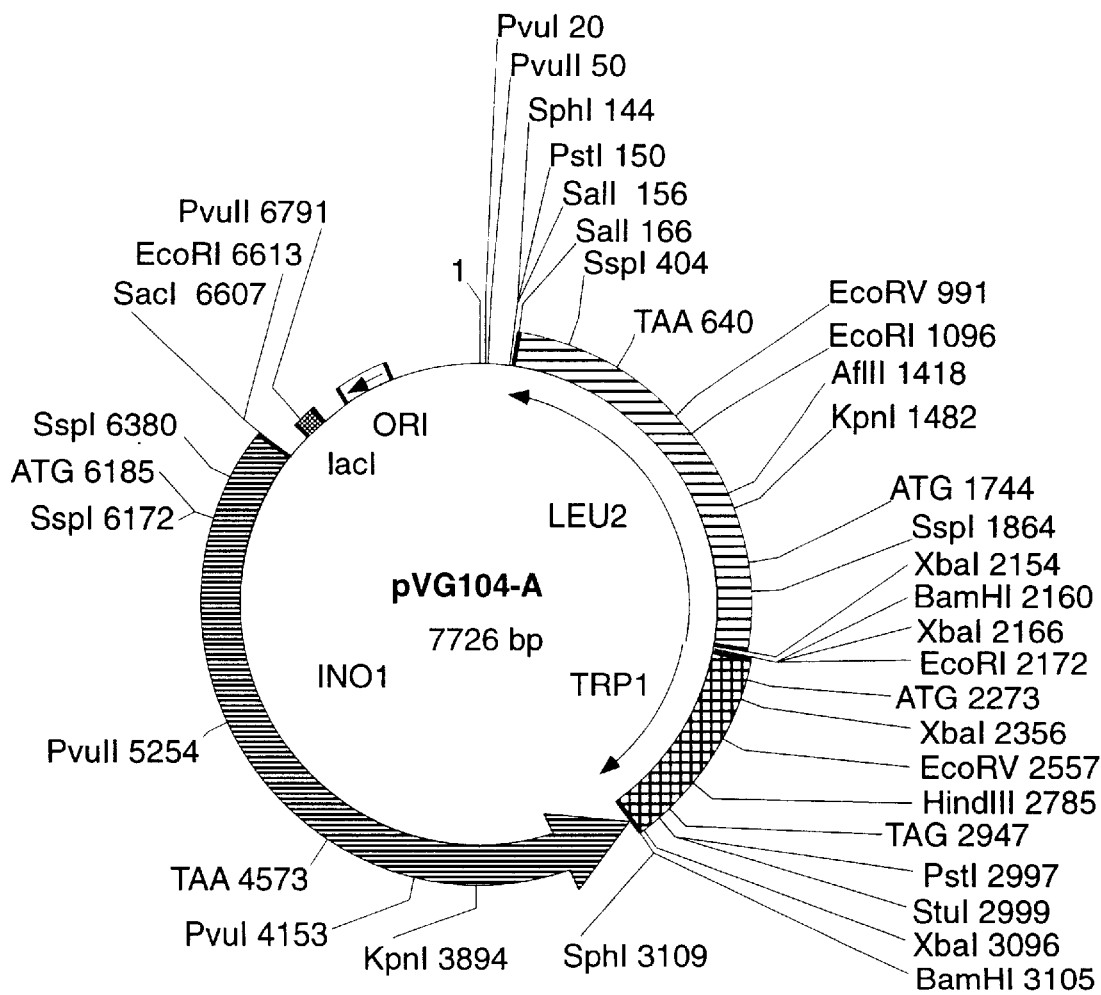
FIG. 8 is a schematic representation of yeast integration plasmid pVG104-A.
Figure 9:
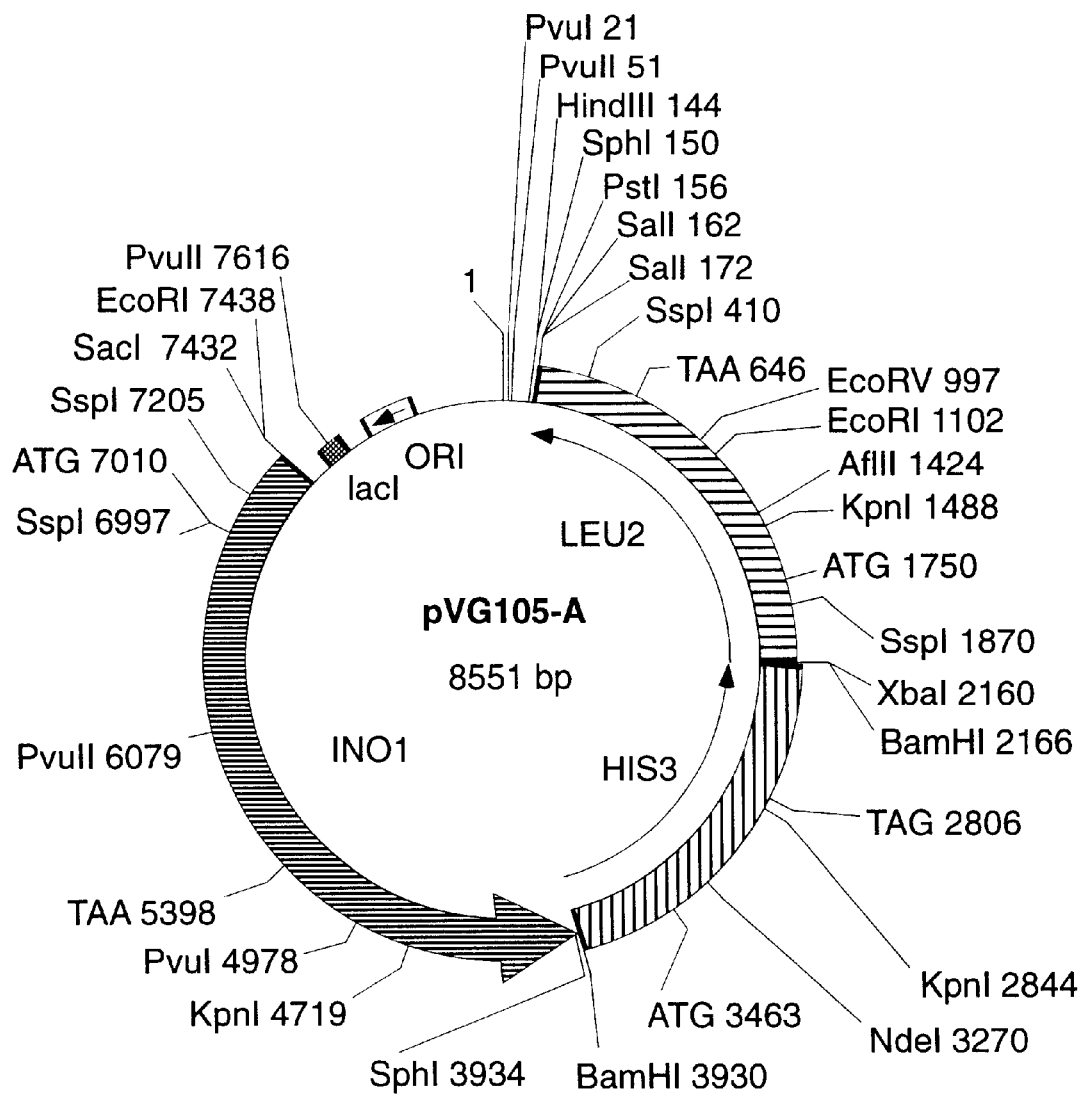
FIG. 9 is a schematic representation of yeast integration plasmid pVG105-A.
Figure 10:
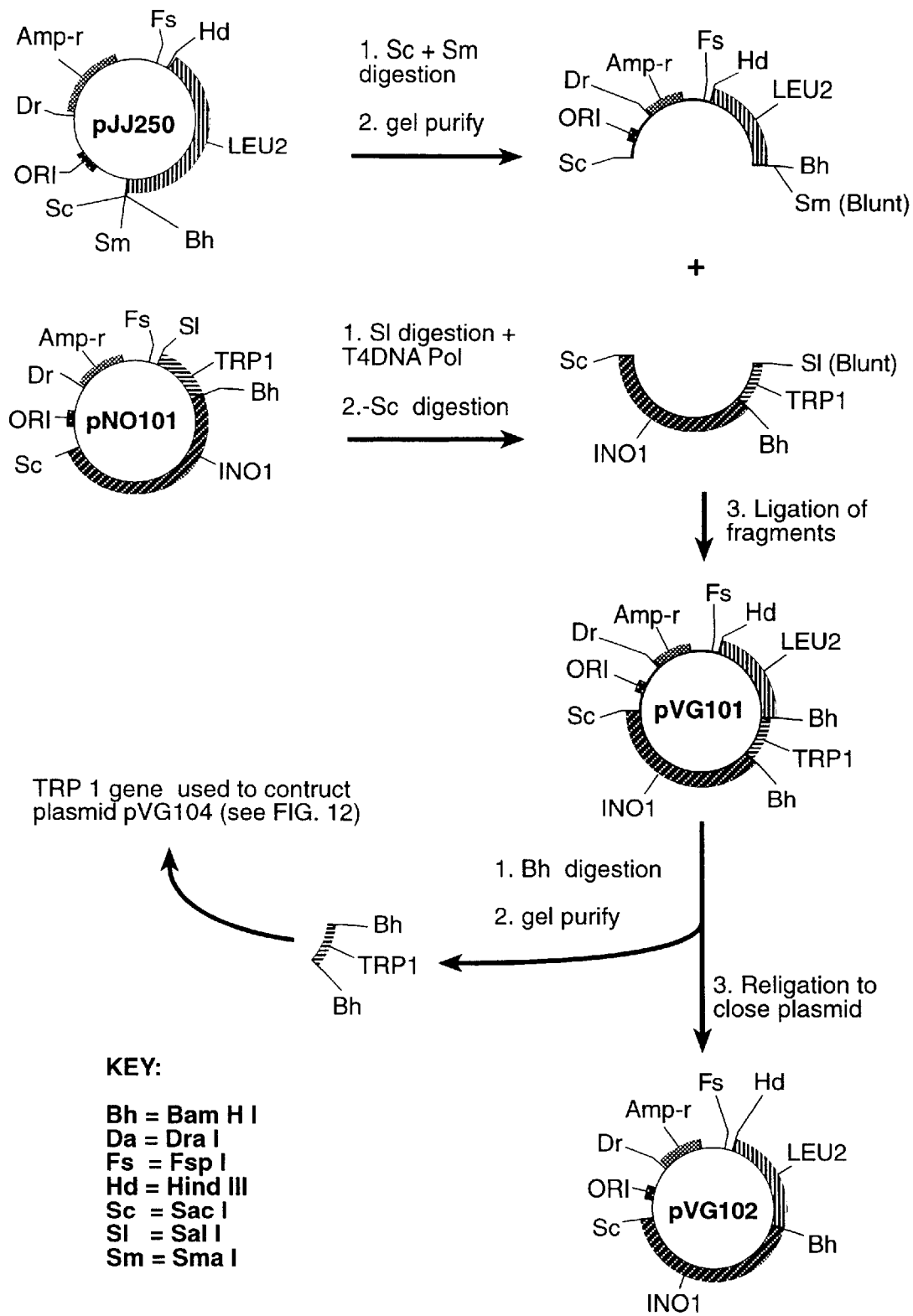
FIGS. 10–13 are schematic representations showing the construction of the yeast integration plasmids of FIGS. 1–9 used in the present invention.
Figure 11:
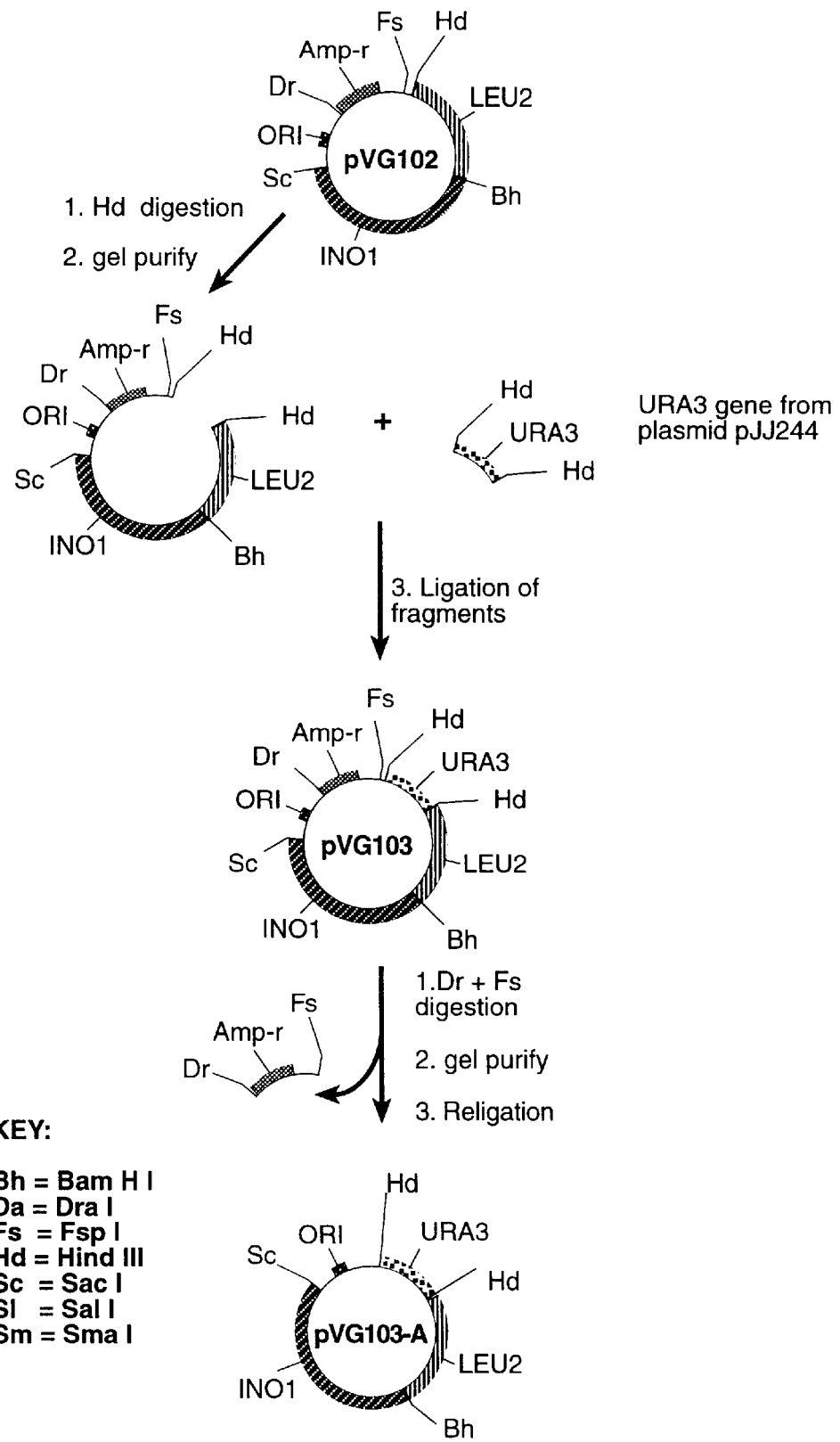
Figure 12:
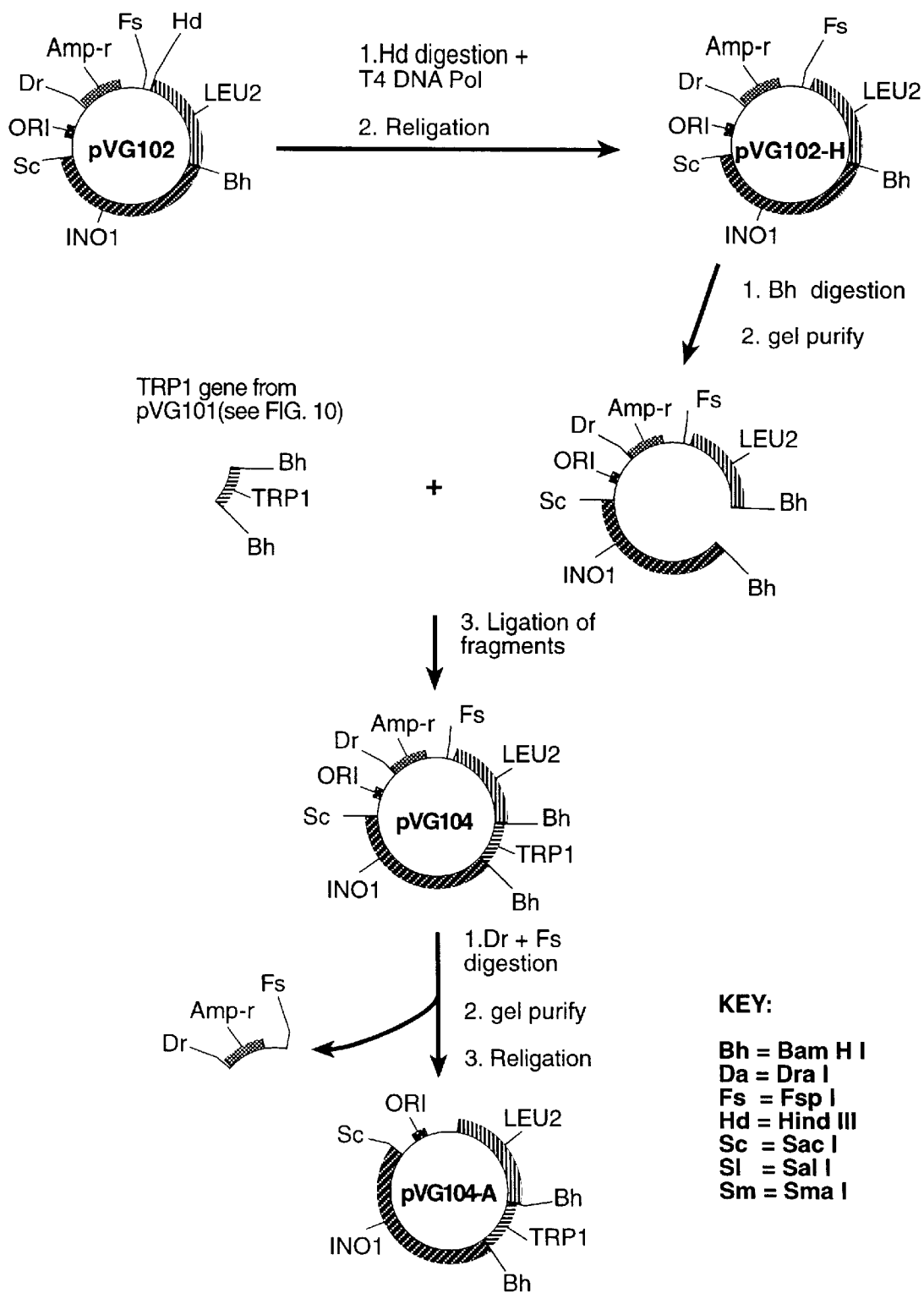
Figure 13:
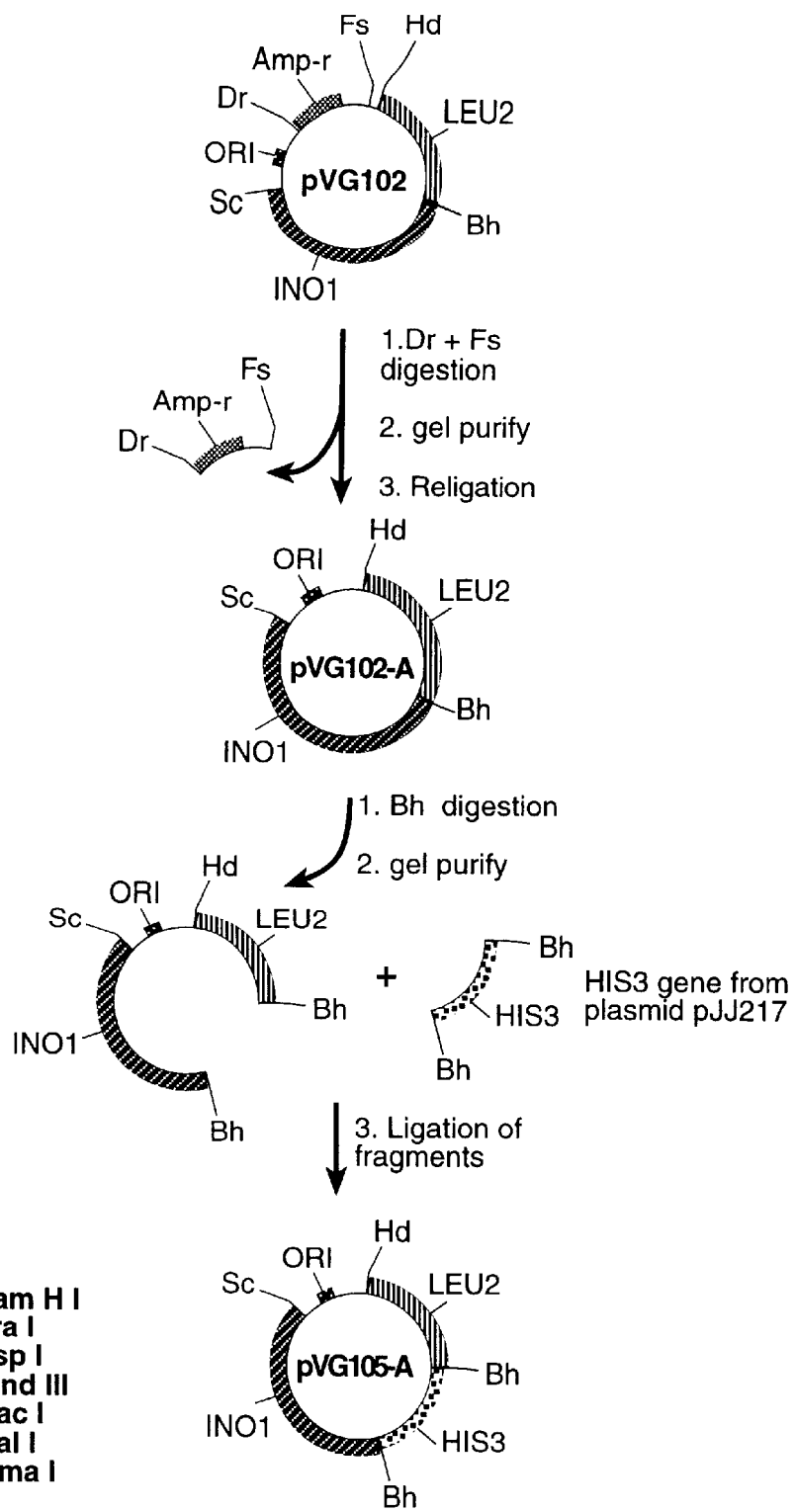

Construction of yeast integration plasmids containing the INO1 gene, was performed as follows (see also FIGS. 10–13). A Sal I/Sac I DNA fragment from plasmid pNO101 containing the TRP1 and INO1 genes was prepared by cutting the pNO101 plasmid first with Sal I, then by treating with T4 DNA polymerase to transform the sticky ends to blunt sites. The DNA fragment was then excised from the rest of the plasmid by digestion with Sac I. The resulting fragment was then gel purified by agarose gel electrophoresis and inserted in the multicloning site of plasmid pJJ250 between the Sac I and Sma I sites to produce the plasmid pVG101 (FIG. 1). A Bam H I/Bam H I DNA fragment containing the TRP1 gene was excised from the pVG101 yeast integration plasmid and the remaining plasmid was religated to produce a derivative plasmid, pVG102 (FIG. 2). As shown schematically in FIG. 12, a further derivative of pVG102 without a Hind III site was prepared by digesting the plasmid pVG102 with Hind III enzyme, making the sites blunt by treatment with T4 DNA polymerase and religating it to produce the pVG102-H plasmid (FIG. 3). As shown in FIG. 11, a Hind III/Hind III DNA fragment from plasmid pJJ244 containing the URA3 gene was inserted in the Hind III site of plasmid pVG102 to produce pVG103 (FIG. 5). As shown in FIG. 12, a Bam H I/Bam H I DNA fragment containing the TRP1 gene from pVG101 was inserted into the BamH I site of plasmid pVG102-H to produce plasmid pVG104 (FIG. 7). A Dra I/Fsp I DNA fragment containing the amp$^r$ gene was excised from plasmids pVG102 (FIG. 2), pVG103 (FIG. 5) and pVG104 (FIG. 7) to produce the derivative plasmids without drug resistance genes namely, pVG102-A (FIG. 4), pVG103-A (FIG. 6) and pVG104-A (FIG. 8) respectively. As shown in FIG. 13, finally a BamH I/BamH I DNA fragment containing the HIS3 gene from plasmid pJJ217 was inserted into the BamH I site of plasmid pVG102-A to produce plasmid pVG105-A (FIG. 9). In yeast integration plasmids pVG102-A (FIG. 4), 103-A (FIG. 6), 104-A (FIG. 8), and 105-A (FIG. 9) described herein were mapped with restriction enzymes to confirm the absence of the amp$^r$ gene and optionally a PCR amplification was carried out to confirm the absence of the amp$^r$ gene.

Yeast transformations with yeast integration plasmids by homologous recombination were performed by first digesting and linearizing the yeast integration plasmids. Plasmid pVG103-A (FIG. 6) was digested with restriction enzyme Sca I that cuts within the URA3 ORF of the targeting gene marker of the plasmid. Plasmid pVG104-A (FIG. 8) was digested with Hind III that cuts within the TRP1 ORF of the targeting gene marker of the plasmid. Plasmid pVG105-A (FIG. 9) was digested with Nde I that cuts within the HIS3 ORF of the targeting gene marker. Similarly, if the yeast leu2 target gene mutation was to be targeted for recombination with the plasmid pVG102-A, this plasmid could be linearized by digestion with a restriction enzyme such as Afl II that cuts within the LEU2 ORF of the targeting gene marker of the plasmid. Similarly, other targeting gene markers such as ADE2, LYS1 and MET15 can be digested and linearized with restriction enzymes that cut within the ORFs of these genes.

The following methods referred to as "Opi test" or "Opi bio-assay" were used to assay for the Opi$^-$ [Over Production of Inositol] phenotype:

1. Strains of *S. cerevisiae* were tested for the Opi$^-$ phenotype by a modification of the method first described by Greenberg, M., et al., *Mol. Gen. Genet.* 186: 157 (1982) and Greenberg, M. L., et al., *Genetics* 100(1): 19 (1982), the disclosures of which are incorporated herein by reference.

Figure 14A:
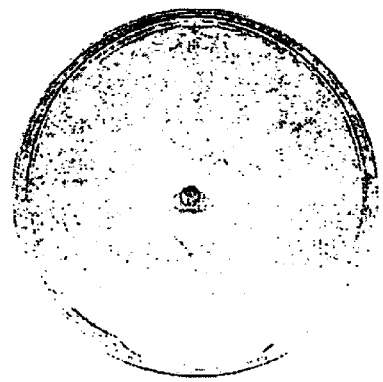
FIGS. 14A–14D are photographs of plate Opi test assays showing the W303 wild-type diploid strain (control) (FIG. 14A); the JAG1 diploid strain (Opi⁻ phenotype) containing two endogenous copies of the INO1 gene (FIG. 14B); the YS3 diploid strain containing up to six copies of the INO1 gene and two to four copies of the bacterial amp$^r$ marker gene (FIG. 14C); and the MVY41O diploid strain (Opi⁻ phenotype) containing eight total copies of the INO1 gene (FIG. 14D). Overproduction and excretion of inositol by strains results in growth in media lacking inositol of the AID indicator strain as observed by a halo around the patch of cells being tested.
Figure 14B:
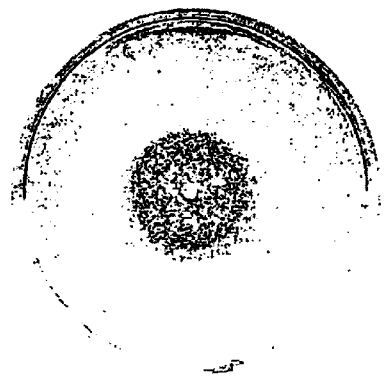
Figure 14C:
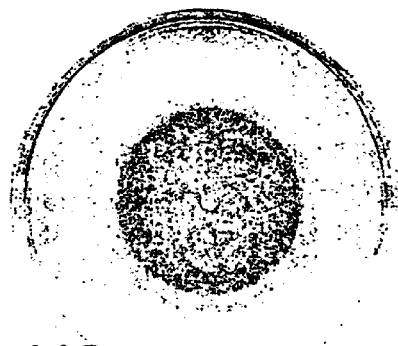
Figure 14D:
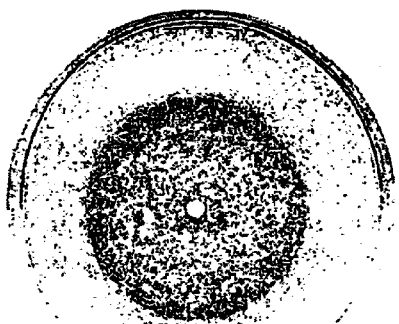

2. Strains to be tested were patched onto I$^-$ plates and, after a 24-hour incubation period, the plates were sprayed with a suspension of a tester strain (AID) in sterile distilled water. The tester strain AID that was used is a diploid homozygous for an ade1 gene marker, which confers a red phenotype and also homozygous for the ino1 gene marker, which confers an inositol auxotrophy (Table 1). Overproduction and excretion of inositol by the assayed strains in media lacking inositol results in growth of the tester strain after 24 hours of the spraying as seen by a red halo of growth around the patch of cells being tested as seen in FIGS. 14A–14D. FIG. 14A is a wild-type control, the W303 diploid strain; FIG. 14B is the JAG1 diploid strain (Opi$^-$ phenotype) containing two endogenous copies of the INO1 gene; FIG. 14C is the YS3 diploid strain containing up to six copies of the INO1 gene and two to four copies of the bacterial amp$^r$ marker gene; and FIG. 14D is the MVY410 diploid strain (Opi$^-$ phenotype) containing eight total copies of the INO1 gene.

In order to construct the JAG1 mutant strain (see Table 1) (FIG. 14D), a yeast strain such as OP-Δ2, mating type "a" (described in Table 1 of U.S. Pat. Nos. 5,529,912 and 5,599,701), was crossed to a W303 mating type "α" haploid (Yeast Genetic Stock Center, Dept. of Molecular Biology and Cell Biology, University of California, Berkeley) (same genotype as W303-1A described in Table 1 of U.S. Pat. Nos. 5,529,912 and 5,599,701, but mating type "α"). The resulting diploid was grown and selected in a media similar to the complete synthetic media described above but which lacked leucine, tryptophan and uracil. Histidine must be present in the medium since the resulting diploid is homozygous for the mutated his3 gene.

The resulting diploid from the above crossing procedure was then sporulated, its tetrads dissected, and the desired haploid spores or ascospores of both mating types containing the mutated genes his3, trp1, and ura3 were colony purified in selective media without any histidine, tryptophan, or uracil. Standard procedures for sporulation, tetrad dissection, and colony purification of haploid spores are described, for example, by Sherman, et al. (1978) and by Guthrie, et al. (1991). The selected spores were assayed with the Opi test described above. The desired spores were the JAG1 haploids MATa and MATα. These are the parent host haploid strains used.

If it is desired to begin the preparation of the JAG1 parent haploids of opposite mating types with auxotrophic markers his3, trp1, and ura3 one could first sporulate the JAG1 diploid (Table 1) (ATCC No. PTA-1065), dissect its asci or tetrads, and isolate and colony purify the haploid spores of opposite mating types by standard methods described, for example, by Sherman, et al. (1978) and Guthrie et al. (1991).

Each of the JAG1 haploid strains, MATa and MATα were then transformed sequentially with the linearized integration plasmids pVG103-A, pVG104-A, and pVG105-A described above using the lithium acetate method described by Ito, H., et al., *J. Bacteriol.* 153: 163 (1983) as modified by Hirsch, J. P., et al., *Mol. Cell. Biol.* 6: 3320 (1986), the disclosure of which is incorporated herein by reference.

After each plasmid integration, the haploids that have taken up and have stably integrated a yeast integration plasmid were colony purified and grown in a selective media lacking the auxotrophic nutrient that was needed by the auxotrophic haploid strain before transforming it with such yeast integration plasmid. This colony purification procedure was done before the next plasmid transformation was carried out. At the end of all transformations a final selection step was used to confirm the prototrophic phenotype of each of the mating type haploids by growing them in minimum media lacking all auxotrophic nutrients.

The last steps were the crossing of the resulting prototrophic haploids of opposite mating types described above by known methods in the art (see also, Guthrie, et al. (1991)), growing the diploid in complete media, and confirming the overproduction of inositol by the Opi test. This final prototrophic diploid containing eight total copies of the INO1 gene (two endogenous copies and six integrated copies) is named MVY410 which is shown in FIG. 14D as excreting more inositol than the YS3 strain shown in FIG. 14C.

The MVY410 diploid strain can be used to produce inositol by employing a fermentation procedure such as that described in U.S. Pat. No. 5,296,364 and U.S. Pat. No. 5,626,847.

Although the invention has been described in detail for the purposes of illustration, it is to be understood that such detail is solely for that purpose and that variations can be made thereon by those skilled in the art without departing from the spirit and scope of the invention except as it may be limited by the claims.

We claim:

1. A method of stably inserting at least one gene of interest into a specific locus in the genome of a host haploid yeast cell without adding any expressed bacterial sequences to said host to form a genetically modified diploid, comprising:

constructing host haploid yeast strains of opposite mating types to contain a non-lethal, selectable gene mutation, a target gene mutation, in at least one gene of either of said haploids;

constructing at least one or a suite of a plurality of yeast integration plasmids, wherein each member plasmid comprises, a selection gene marker which allows for replication of said plasmid in a bacterial plasmid amplification host and for selection of the transformed colonies of said host; a targeting gene marker for directing the insertion of said plasmid into a specific mutated homologous locus, a target gene mutation, in said host yeast genome; a gene of interest that is desired to be expressed in said host yeast; and a bacterial origin of DNA replication functional in said bacterial plasmid amplification host, such that said yeast integration plasmids contain neither any expressed bacterial sequence nor any yeast origin of replication;

amplifying each of said yeast integration plasmids in said plasmid amplification host wherein said plasmid amplification host has a selectable phenotype which is complemented by the selection gene marker of said yeast integration plasmid upon its transformation into said plasmid amplification host;

purifying said amplified yeast integration plasmids;

transforming opposite mating types of said host yeast haploids with yeast integration plasmids such that a targeting gene marker of a yeast integration plasmid directs the integration of said integration plasmid to said target gene mutation in said host to which it is homologous; and mating the transformed haploid yeast cells of opposite mating types to form a diploid cell.

2. The method of claim 1, wherein each integration plasmid member of said suite of plasmids carries a targeting gene marker which is homologous to each target gene mutation in said host yeast such that a specific target gene mutation in said host yeast causes a selectable phenotype in said host which can be rescued by said targeting gene marker carried by each integration plasmid member.

3. The method of claim 2, wherein said target gene mutation in said host yeast comprises no, any or all gene mutations in a gene of the amino acid biosynthetic pathways of said host and no, any or all gene mutations in a gene of the nucleotide biosynthetic pathways of said host wherein said mutation is selectable and non-lethal to said host.

4. The method of claim 3, wherein said mutations of the amino acid biosynthetic pathways of said host comprise his3, leu2, lys1, met15, and trp1.

5. The method of claim 3, wherein said mutations of the nucleotide biosynthetic pathways of said host comprise ade2 and ura3.

6. The method of claim 1, wherein said selection gene marker in said yeast integration plasmids is a yeast gene that complements a selectable and nonlethal mutation in said bacterial plasmid amplification host.

7. The method of claim 6, wherein said bacterial plasmid amplification host is auxotrophic for leucine.

8. The method of claim 7, wherein said bacterial host is *E. coli* JA221.

9. The method of claim 7, wherein said selection gene marker in said yeast integration plasmids comprises the yeast LEU2 gene.

10. The method of claim 8, wherein said selection gene marker in said yeast integration plasmids comprises the yeast LEU2 gene.

11. The method of claim 6, wherein said bacterial plasmid amplification host is auxotrophic for leucine, tryptophan, and uracil.

12. The method of claim 11, wherein said selection gene marker in said yeast integration plasmids is selected from the group consisting of S. cerevisiae LEU2, TRP1, and URA3.

13. The method of claim 1, wherein said gene of interest is the same gene in all member yeast integration plasmids of said suite.

14. The method of claim 1, wherein said gene of interest is not the same gene in each of the member yeast integration plasmids of said suite.

15. The method of claim 1, wherein said gene of interest is INO1.

16. The method of claim 1, wherein said host yeast is of the genus Saccharomyces.

17. The method of claim 1, wherein said host yeast is of the genus Saccharomyces with an Opi⁻ phenotype and has mutated his3, trp1 and ura3 genes as target gene mutations which cause auxotrophies in said host for histidine, tryptophan, and uracil, respectively, and each haploid mating type of said host is sequentially transformed by a suite of yeast integration plasmids wherein a yeast integration plasmid of said suite comprises: a selection gene marker which is LEU2; a targeting gene marker which is HIS3 for one member plasmid of said suite; a targeting gene marker which is TRP1 for another member plasmid of said suite; and a targeting gene marker which is URA3 for another member plasmid of said suite; a gene of interest which is INO1; and an origin of DNA replication which is bacterial ORI.

18. A yeast integration plasmid, comprising:
   a selection gene marker;
   a targeting gene marker;
   a gene of interest; and
   a bacterial origin of DNA replication, wherein said plasmid contains neither any expressed bacterial sequence nor any yeast origin of replication.

19. The yeast integration plasmid of claim 18, wherein said selection gene marker allows for the replication of said plasmid in a bacterial plasmid amplification host and also allows for selection of the transformed bacterial host colonies containing said integration plasmid.

20. The yeast integration plasmid of claim 19, wherein said selection gene marker is a gene that complements a selectable and nonlethal mutation in said bacterial plasmid amplification host.

21. The yeast integration plasmid of claim 20, wherein said selection gene marker complements a leucine auxotrophy in said bacterial plasmid amplification host.

22. The yeast integration plasmid of claim 21, wherein said selection gene marker comprises the LEU2 S. cerevisiae gene.

23. The yeast integration plasmid of claim 18, wherein said targeting gene marker directs the stable integration of said integration plasmid into a specific target gene mutation in a host yeast which causes aselectable phenotype in said host and further wherein said target gene mutation is homologous to said targeting gene marker.

24. The yeast integration plasmid of claim 23, wherein said targeting gene marker is a gene which codes for enzymes in the amino acid biosynthetic pathways of said host yeast or is a gene which codes for enzymes in the nucleotide biosynthetic pathways which complement an auxotrophy in said host yeast.

25. The yeast integration plasmid of claim 23, wherein said targeting gene marker comprises any or all of HIS3, LEU2, LYS1, MET15, TRP1, ADE2, and URA3 yeast genes.

26. The yeast integration plasmid of claim 18, wherein said gene of interest is a gene that is to be expressed in a host yeast and is the same in all plasmid members of a suite of yeast integration plasmids.

27. The yeast integration plasmid of claim 18, wherein said gene of interest is a gene that is to be expressed in a host yeast and is not the same in each plasmid member of a suite of yeast integration plasmids.

28. The yeast integration plasmid of claim 26, wherein said gene of interest is homologous to a gene in the host yeast.

29. The yeast integration plasmid of claim 27, wherein said gene of interest is homologous to a gene in the host yeast.

30. The yeast integration plasmid of claim 18, wherein said origin of DNA replication is a bacterial origin of DNA replication that allows for episomal replication of said integration plasmid in a bacterial plasmid amplification host.

31. The yeast integration plasmid of claim 30, wherein said bacterial origin of DNA replication is ORI from pUC18.

32. The yeast integration plasmid of claim 22, wherein said targeting gene marker is selected from the group consisting of HIS3, TRP1, and URA3 yeast genes, said gene of interest which codes for inositol-1-phosphate synthase, and said origin of DNA replication is the bacterial ORI sequence.

33. The yeast integration plasmid of claim 32, wherein said gene of interest is INO1.

34. The yeast integration plasmid of claim 18, wherein said selection gene marker and said targeting gene marker comprise a LEU2 yeast gene.

35. The yeast integration plasmid of claim 18, wherein said selection gene marker, said targeting gene marker, and said gene of interest are all yeast genes.

36. The yeast integration plasmid of claim 35, wherein said yeast genes are of the genus Saccharomyces.

37. A method of producing inositol, inositol-containing metabolites, phospholipids, phosphatidyl inositol, and other metabolites thereof, comprising the steps of:
   a) constructing haploid host yeasts of the genus Saccharomyces of each mating type which contain an Opi⁻ phenotype which contains one or more target gene mutations in their genome which are non-lethal to said host and which are selectable;
   b) constructing one or more yeast integration plasmids such that the plasmids will be inserted to corresponding target gene mutation loci in said host, wherein each yeast integration plasmid comprises: a selection gene marker; a targeting gene marker; a gene of interest that is expressed in said host; and a bacterial origin of DNA replication, such that said integration plasmids neither contain any expressed bacterial sequence nor any yeast origin of replication;
   c) amplifying episomally each yeast integration plasmid in a bacterial plasmid amplification host microorganism;
   d) purifying the amplified yeast integration plasmids from step c);
   e) sequentially transforming said host yeast with each of the yeast integration plasmids such that each of the said integration plasmids is directed to a specific target gene mutation at each target loci in each of the haploid host cells;

f) optionally mating the transformed host haploids of opposite mating types to form diploids; and g) fermenting the resulting genetically modified yeast from step e) or step f) to produce inositol, inositol-containing metabolites, phospholipids, phosphatidyl inositol and other metabolites.

38. The method of claim 37, wherein said target gene mutations in said haploid host yeasts comprise any or all of ade2, his3, leu2, lys1, met15, trp1, and ura3.

39. The method of claim 37, wherein said target gene mutations in said haploid host yeasts comprise any or all of his3, trp1, and ura3.

40. The method of claim 39, wherein said target gene mutations in said haploid host yeasts additionally comprise leu2.

41. The method of claim 37, wherein said targeting gene markers in said yeast integration plasmids comprise any or all of ADE2, HIS3, LEU2, LYS1, MET15, TRP1, and URA3.

42. The method of claim 37, wherein said targeting gene markers in said yeast integration plasmids comprise any or all of HIS3, TRP1, and URA3.

43. The method of claim 42, wherein said targeting gene markers in said yeast integration plasmids additionally comprise LEU2.

44. The method of claim 37, wherein said plasmid amplification host microorganism is *E. coli* JA221.

45. The method of claim 37, wherein said diploids of step f) are prototrophic.

46. A method of stably inserting at least one gene of interest into a specific locus in the genome of a host haploid yeast without adding any expressed bacterial sequences to said host to form a genetically modified haploid cell, comprising:

constructing host haploid yeast strains to contain a non-lethal, selectable gene mutation, a target gene mutation, in at least one gene of said haploid;

constructing at least one or a suite of a plurality of yeast integration plasmids, wherein each member plasmid comprises, a selection gene marker which allows for replication of said plasmid in a bacterial plasmid amplification host and for selection of the transformed colonies of said host; a targeting gene marker for directing the insertion of said plasmid into a specific mutated homologous locus, a target gene mutation, in said host yeast genome; a gene of interest that is desired to be expressed in said host yeast; and a bacterial origin of DNA replication functional in said bacterial plasmid amplification host, such that said yeast integration plasmids contain neither any expressed bacterial sequence nor any yeast origin of replication;

amplifying each of said yeast integration plasmids in said plasmid amplification host wherein said plasmid amplification host has a selectable phenotype which is complemented by the selection gene marker of said yeast integration plasmid upon its transformation into said plasmid amplification host;

purifying said amplified yeast integration plasmids; and transforming of said host yeast haploids of either or both mating types with yeast integration plasmids such that a targeting gene marker of a yeast integration plasmid directs the integration of said integration plasmid to said target gene mutation in said host to which it is homologous.

47. The method of claim 46, wherein each integration plasmid member of said suite of plasmids carries a targeting gene marker which is homologous to each target gene mutation in said host yeast such that a specific target gene mutation in said host yeast causes a selectable phenotype in said host which can be rescued by said targeting gene marker carried by each integration plasmid member.

48. The method of claim 47, wherein said target gene mutation in said host yeast comprises no, any or all gene mutations in a gene of the amino acid biosynthetic pathways of said host and no, any or all gene mutations in a gene of the nucleotide biosynthetic pathways of said host wherein said mutation is selectable and non-lethal to said host.

49. The method of claim 48, wherein said mutations of the amino acid biosynthetic pathways of said host comprise his3, leu2, lys1, met15, and trp1.

50. The method of claim 49, wherein said mutations of the nucleotide biosynthetic pathways of said host comprise ade2 and ura3.

51. The method of claim 46, wherein said selection gene marker in said yeast integration plasmids is a yeast gene that complements a selectable and nonlethal mutation in said bacterial plasmid amplification host.

52. The method of claim 47, wherein said bacterial plasmid amplification host is auxotrophic for leucine.

53. The method of claim 52, wherein said bacterial host is *E. coli* JA221.

54. The method of claim 52, wherein said selection gene marker in said yeast integration plasmids comprises the yeast LEU2 gene.

55. The method of claim 53, wherein said selection gene marker in said yeast integration plasmids comprises the yeast LEU2 gene.

56. The method of claim 51, wherein said bacterial plasmid amplification host is auxotrophic for leucine, tryptophan, and uracil.

57. The method of claim 1, wherein said selection gene marker in said yeast integration plasmids is selected from the group consisting of *S. cerevisiae* LEU2, TRP1, and URA3.

58. The method of claim 46, wherein said gene of interest is the same gene in all member yeast integration plasmids of said suite.

59. The method of claim 46, wherein said gene of interest is not the same gene in each of the member yeast integration plasmids of said suite.

60. The method of claim 46, wherein said gene of interest is INO1.

61. The method of claim 46, wherein said host yeast is of the genus Saccharomyces.

62. The method of claim 46, wherein said host yeast is of the genus Saccharomyces with an Opi$^-$ phenotype and has mutated his3, trp1 and ura3 genes as target gene mutations which cause auxotrophies in said host for histidine, tryptophan, and uracil, respectively, and each haploid cell of said host is sequentially transformed by a suite of yeast integration plasmids wherein a yeast integration plasmid of said suite comprises: a selection gene marker which is LEU2; a targeting gene marker which is HIS3 for one member plasmid of said suite; a targeting gene marker which is TRP1 for another member plasmid of said suite; and a targeting gene marker which is URA3 for another member plasmid of said suite; a gene of interest which is INO1; and an origin of DNA replication which is bacterial ORI.

* * * * *